(12) United States Patent
Okano et al.

(10) Patent No.: US 10,512,765 B2
(45) Date of Patent: Dec. 24, 2019

(54) METHOD OF MANUFACTURING SHEET WITH NEEDLE LIKE PROTRUSIONS

(71) Applicant: FUJIFILM Corporation, Tokyo (JP)

(72) Inventors: Keio Okano, Kanagawa (JP); Yoshinobu Katagiri, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 107 days.

(21) Appl. No.: 15/335,436

(22) Filed: Oct. 27, 2016

(65) Prior Publication Data

US 2017/0120026 A1    May 4, 2017

(30) Foreign Application Priority Data

Oct. 28, 2015   (JP) ................ 2015-211803

(51) Int. Cl.
*A61M 37/00*   (2006.01)
*B29C 31/04*   (2006.01)
(Continued)

(52) U.S. Cl.
CPC ....... *A61M 37/0015* (2013.01); *A61K 9/7023* (2013.01); *B29C 31/041* (2013.01);
(Continued)

(58) Field of Classification Search
CPC ... B29C 39/24; B29C 33/3842; B29C 39/003; B29C 39/026; B29C 31/041;
(Continued)

(56) References Cited

U.S. PATENT DOCUMENTS 3,613,167 A    10/1971  Stirrat
3,679,341 A *   7/1972  Graybill .................. B29C 45/23
                                                                                425/159
(Continued)

FOREIGN PATENT DOCUMENTS

EP        2921202       9/2015
JP      2012011579      1/2012
(Continued)

OTHER PUBLICATIONS

"Search Report of European Counterpart Application", dated Mar. 20, 2017, p. 1-p. 6.
(Continued)

*Primary Examiner* — Francisco W Tschen
(74) *Attorney, Agent, or Firm* — JCIPRNET

(57) ABSTRACT

The method includes the steps of: preparing a mold and a liquid filling device; and filling needle-like recessed portions with a liquid medicine by repeating the following: a filling operation in which the liquid medicine is supplied to the mold from the liquid filling device and the needle-like recessed portions are filled with the liquid medicine while a nozzle tip is brought into pressed contact with a surface of the mold; and a moving operation in which a nozzle is relatively moved with respect to the mold while the nozzle tip and the surface of the mold are in contact with each other, wherein the nozzle is held in a Z-axis drive unit configured to vertically move the nozzle while an elastic body is provided in the Z-axis drive unit, while the nozzle tip is brought into pressed contact with the surface of the mold.

10 Claims, 15 Drawing Sheets

(51) Int. Cl.
*B29C 39/24* (2006.01)
*B29C 39/02* (2006.01)
*A61K 9/70* (2006.01)
*B29C 33/38* (2006.01)
*B29C 39/00* (2006.01)
*B29K 105/00* (2006.01)
*B29L 31/00* (2006.01)

(52) U.S. Cl.
CPC ........ *B29C 33/3842* (2013.01); *B29C 39/003* (2013.01); *B29C 39/026* (2013.01); *B29C 39/24* (2013.01); *A61M 2037/0053* (2013.01); *A61M 2207/10* (2013.01); *B29K 2005/00* (2013.01); *B29K 2105/0035* (2013.01); *B29K 2883/00* (2013.01); *B29L 2031/756* (2013.01); *B29L 2031/7544* (2013.01)

(58) Field of Classification Search
CPC .......... A61M 37/0015; A61M 2207/10; A61M 2037/0053; A61K 9/7023; B29K 2105/0035; B29K 2005/00; B29K 2883/00; B29L 2031/756; B29L 2031/7544
See application file for complete search history.

(56) References Cited

U.S. PATENT DOCUMENTS

| | | | | |
|---|---|---|---|---|
| 3,718,524 | A * | 2/1973 | Bright | B29C 33/50 156/246 |
| 5,059,112 | A * | 10/1991 | Wieser | B29C 39/24 264/517 |
| 6,432,333 | B1 * | 8/2002 | Emoto | B29C 45/1777 264/328.11 |
| 2006/0127521 | A1 * | 6/2006 | Toshio | B29C 45/231 425/146 |
| 2008/0102155 | A1 * | 5/2008 | Lindsten | B29C 33/444 425/556 |
| 2015/0238413 | A1 | 8/2015 | Mochizuki et al. | |

FOREIGN PATENT DOCUMENTS

| | | |
|---|---|---|
| JP | 2012171414 | 9/2012 |
| WO | 2014077242 | 5/2014 |

OTHER PUBLICATIONS

"Notification of Reasons for Refusal of Japan Counterpart Application," dated Dec. 26, 2018, with English translation thereof, p. 1-p. 7.

* cited by examiner

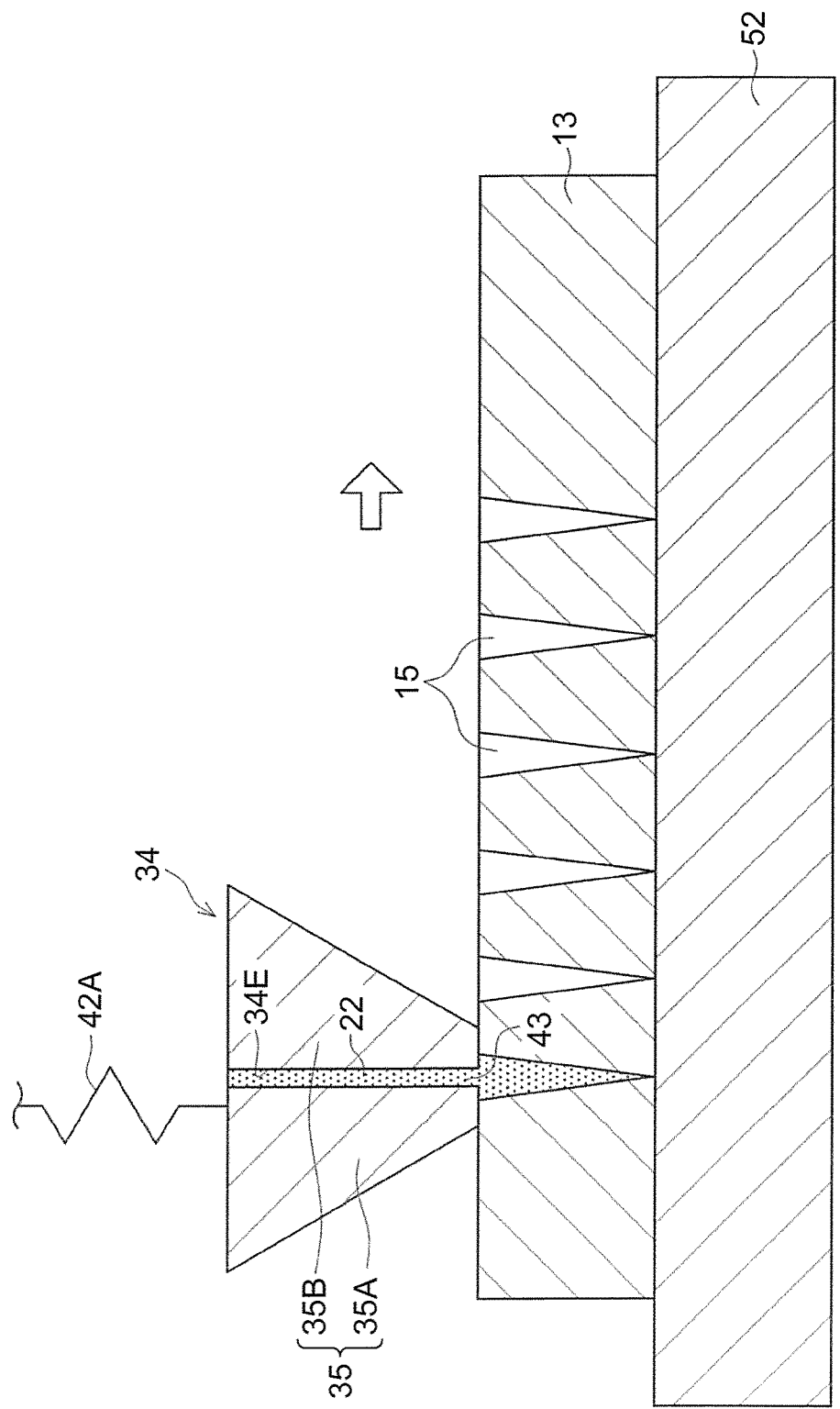

FIG.18

| No. | HOLDING METHOD | THE NUMBER OF REPEATED TIMES [TIMES] | FILLING AMOUNT OF NEEDLE-LIKE RECESSED PORTIONS [mg] |
|---|---|---|---|
| COMPARATIVE EXAMPLE 1 | DIRECT HOLDING | 1 | 3.05 |
| | | 2 | 3.51 |
| | | 3 | 2.64 |
| | | 4 | 2.60 |
| | | 5 | 3.55 |
| EXAMPLE 1 | HOLDING USING LEAF SPRING | 1 | 3.15 |
| | | 2 | 3.09 |
| | | 3 | 2.82 |
| | | 4 | 2.94 |
| | | 5 | 3.21 |

METHOD OF MANUFACTURING SHEET WITH NEEDLE LIKE PROTRUSIONS

CROSS-REFERENCE TO RELATED APPLICATIONS

The present application claims priority under 35 U.S.C. § 119 to Japanese Patent Application No. 2015-211803, filed on Oct. 28, 2015. The above application is hereby expressly incorporated by reference, in its entirety, into the present application.

BACKGROUND OF THE INVENTION

Field of the Invention

The present invention relates to a method of manufacturing a sheet having needle-like protrusions.

Description of the Related Art

In recent years, as an example of a sheet having needle-like protrusions, a transdermal absorption sheet including a plurality of needle-like protrusions (referred to as micro needles) containing a medicine has been used to deliver the medicine into a skin. Typically, the transdermal absorption sheet is pressed on the skin to insert the needle-like protrusions into the skin, and then the medicine in the needle-like protrusions is delivered into the skin.

Various methods have been provided for manufacturing this kind of transdermal absorption sheet. For example, WO 2014/077242A1 discloses a method of filling two-dimensionally arranged needle-like recessed portions with a liquid medicine containing a medicine by repeating the following: a filling operation in which a solution (liquid medicine) containing the medicine is supplied to a mold from a liquid feeder and one or more needle-like recessed portions are filled with the solution containing the medicine while a nozzle tip of a nozzle adjusted to a position above needle-like recessed portions is pressed so as to be brought into contact with a surface of the mold at a desired pressing force; and a moving operation in which the nozzle is moved relatively to the mold while the nozzle tip and the surface of the mold are in contact with each other. This enables the needle-like recessed portions to be efficiently filled with the liquid medicine by discharging only a necessary amount of the liquid medicine while the nozzle is pressed on the surface of the mold. As a result, the medicine can be concentrated into the needle-like protrusions, and transdermal absorption sheets can be manufactured with high production efficiency.

SUMMARY OF THE INVENTION

Unfortunately, the method of manufacturing a transdermal absorption sheet disclosed in WO 2014/077242A1 allows the needle-like recessed portions to be filled with the liquid medicine while the nozzle tip of the nozzle is pressed on the surface of the mold at a desired pressing force (e.g. 1.4 N/cm$^2$), and thus a subsequent problem is found.

Problem of Filling Accuracy

In that filling method, the needle-like recessed portions are filled with the liquid medicine in a state where the mold is crushed by pressing the nozzle tip on the mold. Thus, if a pressing force varies due to a factor, such as a displacement amount by pressing and variation in mold thickness, a volume of each of the arrayed needle-like recessed portions varies, or a total volume of the needle-like recessed portions varies among sheets. As a result, the filling amount of the liquid medicine varies in each of the needle-like recessed portions. In addition, if a pressing angle at which the nozzle is pressed on the mold varies, the volume of each of the needle-like recessed portions also varies to cause variation in the filling amount of the liquid medicine in each of the needle-like recessed portions.

Here, the "displacement amount by pressing" means a distance in a mold thickness direction between the surface of the mold before the nozzle tip is pressed and the surface of the mold which is depressed (displaced) when the nozzle tip is pressed on the surface of the mold. In other words, the "displacement amount by pressing" means the variation amount in the thickness of the mold before and after the nozzle tip is pressed on the surface of the mold.

The present invention is made in light of the above-mentioned circumstances, and aims to provide a method of manufacturing a sheet, capable of improving filling accuracy of liquid for each of needle-like recessed portions.

According to an aspect of the present invention, a method of manufacturing a sheet with needle-like protrusions includes: a preparing step of preparing a mold with needle-like recessed portions, a filling device provided with a liquid feeder having a nozzle that discharges a liquid from a slit-like opening formed at a nozzle tip; and a liquid filling step of filling the needle-like recessed portions with the liquid by repeating a filling operation of supplying the liquid to the mold from the liquid feeder to fill one or more needle-like recessed portions with the liquid while the nozzle tip adjusted to a position above the needle-like recessed portions is brought into pressed contact with a surface of the mold, and a moving operation of moving the nozzle relatively to the mold in a state where the nozzle tip and the surface of the mold are in contact with each other, wherein the liquid filling step includes bringing the nozzle tip into pressed contact with the surface of the mold while the nozzle is held by a Z-axis drive unit configured to vertically move the nozzle, with an elastic body interposed between the Z-axis drive unit and the nozzle.

The filling step of filling the needle-like recessed portions with the liquid includes both an aspect of filling the needle-like recessed portions with the liquid while the nozzle is continuously moved relatively, and an aspect of intermittent movement in which after the nozzle is temporarily stopped above the needle-like recessed portions to be filled with the liquid during relative movement of the nozzle, the nozzle is relatively moved again. Both the aspects have a state where the nozzle tip of the nozzle is in contact with the surface of the mold.

The relative movement of the nozzle to the mold includes both a case of moving the nozzle while the mold is fixed, and a case of moving the mold while the nozzle is fixed.

The present inventers have acquired the following findings in manufacturing of a sheet with needle-like protrusions. That is, a soft material is typically used as a material of the mold to prevent the needle-like protrusions from being damaged, and the needle-like recessed portions of the mold is a reverse mold of the needle-like protrusions, and thus each of the needle-like recessed portions has a shape in which a hole that has a large opening and tapers in a depth direction. When the needle-like recessed portions are filled with the liquid while the nozzle tip is brought into pressed contact with the surface of the mold described above, the mold crashes in a characteristic way as follows: while the front surface of the mold having the needle-like recessed portions, corresponding to a root portion of each of the needle-like protrusions, is preferentially crushed, the whole of the needle-like recessed portions is crushed.

Thus, in order to precisely fill the liquid into the mold whose thickness locally varies due to crushing of the needle-like recessed portion, an amount of crushing of the whole of the needle-like recessed portions needs to be considered while an amount of crushing in the surface of the mold of the needle-like recessed portions, corresponding to the root portion of each of the needle-like protrusions, is particularly and carefully controlled.

As a result, the present inventers have acquired findings that improvement in filling accuracy cannot be sufficiently acquired by only uniformizing the thickness of the crushed mold using a shim, a distance meter, and the like, and by uniformizing an amount of crushing by applying a predetermined load to the nozzle or by feeding back thickness information.

The present invention is made on the basis of the findings described above.

According to the present invention, the nozzle is held by a Z-axis drive unit configured to vertically move the nozzle, with an elastic body interposed between the Z-axis drive unit and the nozzle, and the nozzle tip is brought into pressed contact with the surface of the mold. Accordingly, the elastic body absorbs variation in pressing force by the nozzle due to variation in displacement amount by pressing with the nozzle tip on the surface of the mold; variation in thickness of the mold; variation in a pressing angle, and so on, so as to make the pressing force uniform.

As a result, a problem in conventional art that a volume of each of the needle-like recessed portions varies by factors such as variation in displacement amount by pressing and variation in thickness of the mold are solved, and thus the filling accuracy of the liquid in each of the needle-like recessed portions can be improved.

In the present invention, it is preferable to provide a viscous substance between the Z-axis drive unit configured to vertically move the nozzle and the nozzle. In this case, it is further preferable to provide the elastic body and the viscous substance in parallel.

As the viscous substance, for example, a shock absorber including a rubber bag filled with liquid or gas, a high molecular material with viscous force, or the like, can be suitably applied.

In the present invention, while there is available any kind of elastic body as long as the elastic body is deformed when force is applied thereto, and has a restoring force allowing the elastic body to be restored to an original shape when the force is removed. It is preferable to use an elastic body having elastic force against translational movement in a thickness direction of the mold, or an elastic body having both the elastic force against the translational movement in the thickness direction of the mold, and elastic force against in-plane rotation including a direction of relative movement between the nozzle and the mold.

It is preferable to use a coil spring as the elastic body having the elastic force against the translational movement in the thickness direction of the mold. Other than the coil spring, an extension spring, a disk spring, a resin having elastic force, an air spring, and an elastic body being a combination of them, are available.

It is preferable to use a leaf spring as the elastic body having both the elastic force against the translational movement in the thickness direction of the mold, and the elastic force against the in-plane rotation (mainly rotation in a horizontal plane) including the direction of the relative movement between the nozzle and the mold. Other than the leaf spring, a torsion spring, a resin spring, and an elastic body being a combination of them, are available.

In the present invention, it is preferable to further provide a guide mechanism for regulating a movable range of the nozzle in a movement direction.

It is preferable that the sheet in the present invention is a transdermal absorption sheet with needle-like protrusions containing a medicine.

According to another aspect of the present invention, a method of manufacturing a sheet with needle-like protrusions includes: a preparing step of preparing a mold with needle-like recessed portions, a filling device provided with a liquid feeder having a nozzle that discharges a liquid from a slit-like opening formed at a nozzle tip; and a liquid filling step of filling the needle-like recessed portions with the liquid by repeating a filling operation of supplying the liquid to the mold from the liquid feeder to fill one or more needle-like recessed portions with the liquid while the nozzle tip adjusted to a position above the needle-like recessed portions is brought into pressed contact with a surface of the mold, and a moving operation of moving the nozzle relatively to the mold in a state where the nozzle tip and the surface of the mold are in contact with each other, wherein the mold is placed on a base provided with an elastic body, and the liquid filling step includes bringing the nozzle tip into pressed contact with the surface of the mold by a Z-axis drive unit configured to vertically move the nozzle.

An aspect of providing the elastic body in the base includes forming the base of a resin having elastic force, and providing an elastic body such as a coil spring between a plurality of plates that constitutes the base.

According to the method of manufacturing a sheet of the present invention, filling accuracy of liquid in each of the needle-like recessed portions can be improved.

BRIEF DESCRIPTION OF THE DRAWINGS

FIG. 12 illustrates a relationship between the nozzle and the mold in filling operation in a liquid filling step;

FIG. 18 is a table showing results of examples.

DETAILED DESCRIPTION OF THE EMBODIMENTS

Figure 1:
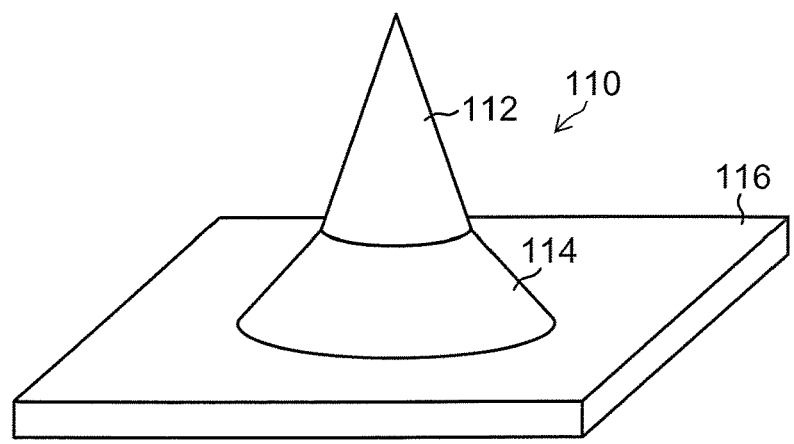
FIG. 1 is a partial enlarged view of a transdermal absorption sheet with needle-like protrusions.

Hereinafter, a preferable embodiment of a method of manufacturing a sheet of the present invention will be described with reference to accompanying drawings.

While the method of manufacturing a sheet of the present invention is applicable to manufacturing of every sheet with needle-like protrusions, manufacturing of a transdermal absorption sheet with needle-like protrusions containing a medicine, as an example of the sheet, will be described in the present embodiment.

The present invention will be described according to a preferable embodiment described below. The present invention can be modified by many techniques without departing from the scope of the present invention, and another embodiment other than the present embodiment is available. Thus, all modifications within the scope of the present invention are included in the scope of claims.

In the drawings, a component designated by the same reference numeral is a similar component having a similar function. In addition, in a case where a numeric value range is expressed by using "a lower limit value to an upper limit value" in the present specification, the lower and upper limit values are also included in the numeric value range.

First, an example of the transdermal absorption sheet to be manufactured by the method of manufacturing a sheet of the present embodiment will be described.

Figure 2:
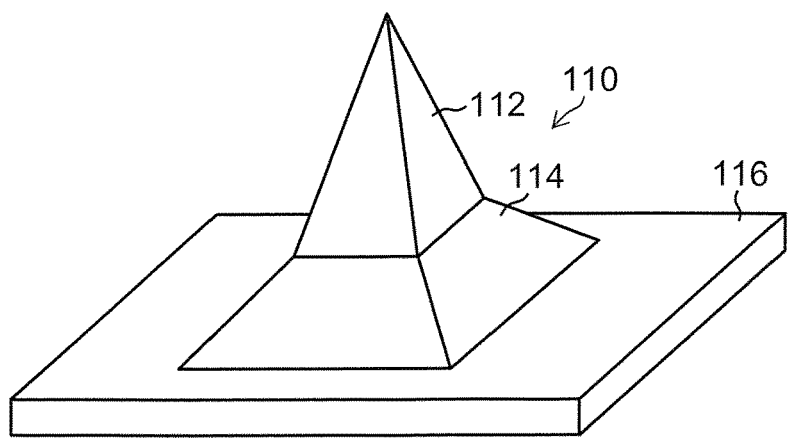
FIG. 2 is a partial enlarged view of a transdermal absorption sheet with needle-like protrusions with a different shape.

FIGS. 1 and 2 each are a partial enlarged view illustrating an example of a transdermal absorption sheet 100, and show a needle-like protrusion 110 (referred to as a micro needle).

The transdermal absorption sheet 100 is attached to a skin to deliver a medicine into the skin. As illustrated in FIG. 1, the transdermal absorption sheet 100 includes a needle section 112 with a tapered shape, a frustum section 114 connected to the needle section 112, and a sheet-like sheet section 116 connected to the frustum section 114. The needle section 112 with a tapered shape and the frustum section 114 constitute the needle-like protrusions 110. The sheet-like shape means a shape which has: two principal surfaces (a first principal surface and a second principal surface) each with a large area, facing each other; and a thin thickness therebetween, and is flat as a whole, and thus the principal surfaces do not need to be completely flat.

In a surface of the sheet section 116, a plurality of frustum sections 114 are formed (only one frustum section 114 is illustrated in FIG. 1). The frustum section 114 has two bottom faces, and has three-dimensional structure surrounded by pyramid faces. One bottom face (lower bottom) with a larger area in the two bottom faces of the frustum section 114 is connected to the sheet section 116. The other bottom face (upper bottom) with a smaller area in the two bottom faces of the frustum section 114 is connected to the needle section 112. That is, an area of the bottom face positioned in a direction away from the sheet section 116 in the two bottom faces of the frustum section 114 decreases.

The needle section 112 has a tapered shape, and the needle section 112 has a shape in which a leading end away from the bottom face with a large area has a minimum area. Since the bottom face with a large area of the needle section 112 is connected to the bottom face with a small area of the frustum section 114, the needle section 112 has a shape tapered in the direction away from the frustum section 114. Thus, the needle-like protrusion 110 including the needle section 112 and the frustum section 114 has a shape tapered toward a leading end from the sheet section 116, as a whole. Four to two thousand five hundred needle-like protrusions 110 are provided on the sheet section 116. The number of the needle-like protrusions 110 is not limited to the numbers above.

In FIG. 1, the frustum section 114 is in the shape of a truncated cone, and the needle section 112 is in the shape of a cone. The needle section 112 has a tip whose shape can be appropriately changed to a curved surface with a curvature radius of 0.01 μm or more and 50 μm or less, a flat surface, or the like, depending on a level of insertion of the needle section 112 into a skin.

FIG. 2 illustrates the needle-like protrusion 110 with another shape. In FIG. 2, the frustum section 114 is in the shape of a quadrangular prismoid, and the needle section 112 is in the shape of a quadrangular pyramid.

Figure 3:
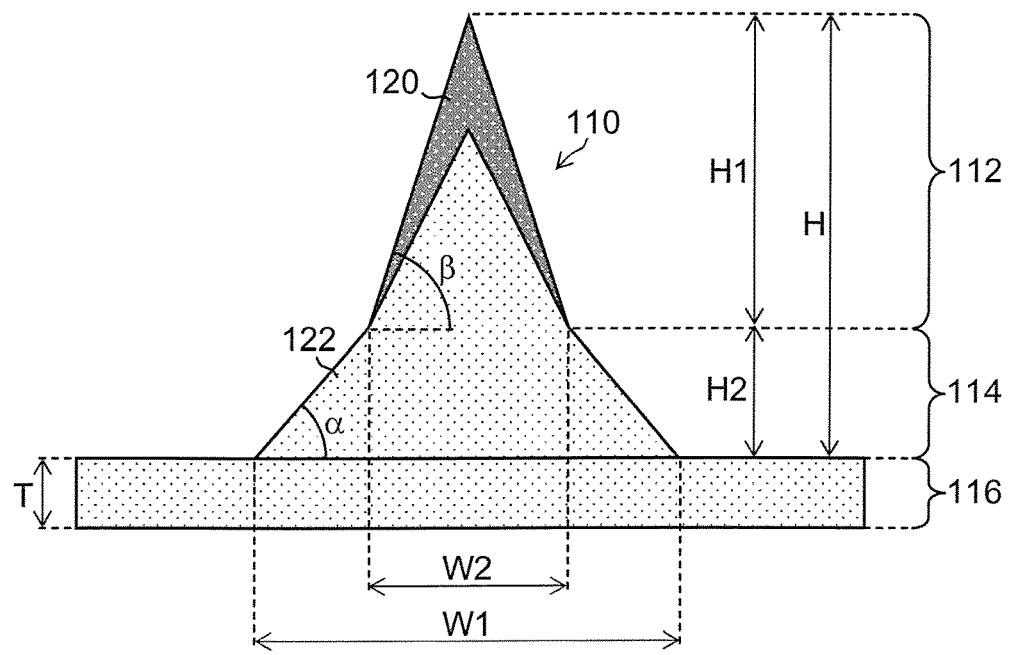
FIG. 3 is a longitudinal sectional view of the needle-like protrusions of the transdermal absorption sheet illustrated in FIGS. 1 and 2.

FIG. 3 is a sectional view of the transdermal absorption sheet 100 illustrated in FIGS. 1 and 2. FIG. 3 illustrates the transdermal absorption sheet 100 that includes a first layer 120 containing a medicine, and a second layer 122 not-containing the medicine, for example. The second layer 122 may contain the medicine, and a needle portion may be formed only in the first layer.

The sheet section 116 has a thickness T that is preferably within a range from 10 μm to 2000 μm, and that is more preferably within a range from 10 μm to 1000 μm. The bottom face (lower bottom) with which the frustum section 114 and the sheet section 116 are in contact has a width W1 that is preferably within a range from 100 μm to 1500 μm, and that is more preferably within a range from 100 μm to 1000 μm. The bottom face (upper bottom) with which the frustum section 114 and the needle section 112 are in contact has a width W2 that is preferably within a range from 100 μm to 1500 μm, and is more preferably within a range from 100 μm to 1000 μm. It is preferable that W1>W2 is satisfied, i.e., the width W1 is larger than the width W2, within each of the numeric value ranges described above.

The needle-like protrusion 110 has a height H that is preferably within a range from 100 μm to 2000 μm, and that is more preferably within a range from 200 μm to 1500 μm. In addition, H1/H2, which is a ratio between a height H1 of the needle section 112 and a height H2 of the frustum section 114, is preferably within a range from 1 to 10, and is more preferably within a range from 1.5 to 8. Further, it is preferable that the height H2 of the frustum section 114 is within a range from 10 μm to 1000 μm.

An angle α between an inclined face of the frustum section 114 and a surface parallel to the surface of the sheet section 116 is preferably within a range from 10° to 60°, and is more preferably within a range from 20° to 50°. In addition, an angle β between an inclined face of the needle section 112 and a surface parallel to the upper bottom of the frustum section 114 is preferably within a range from 45° to 85°, and is more preferably within a range from 60° to 80°.

While the angle β may be equal to the angle α, it is preferable the angle β is more than the angle α, because it makes easy to puncture a skin with the needle-like protrusion 110.

While the transdermal absorption sheets 100 with the needle-like protrusions 110 illustrated in FIGS. 1 and 2 are shown in the present embodiment, the transdermal absorption sheet 100 is not limited to the shapes.

Figure 4:
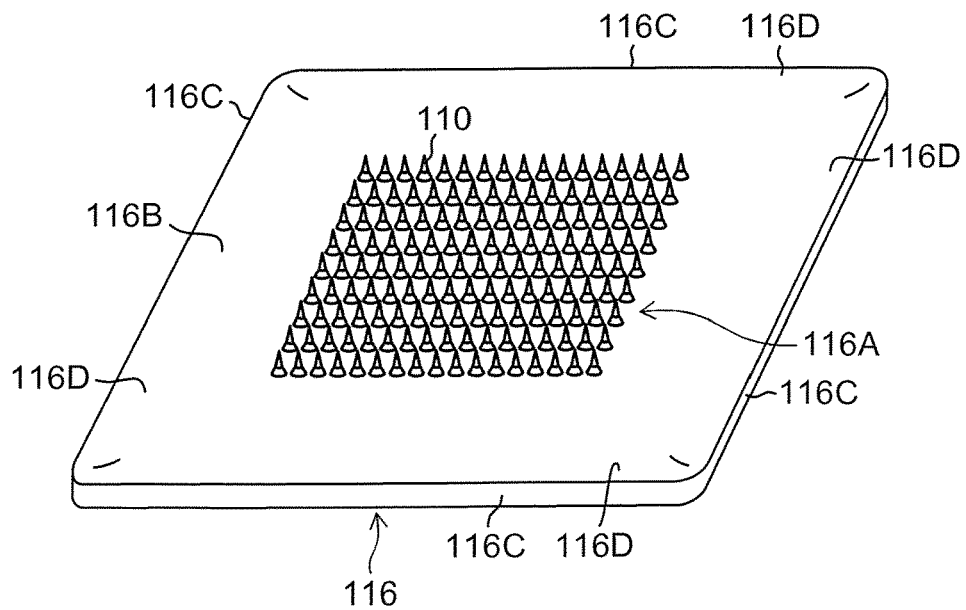
FIG. 4 is a general perspective view of the transdermal absorption sheet.

FIG. 4 is a general perspective view of the transdermal absorption sheet. As illustrated in FIG. 4, the transdermal absorption sheet 100 includes the sheet section 116 having the first principal surface and the second principal surface, and a plurality of needle-like protrusions 110 arranged on the first principal surface of the sheet section 116. The sheet section 116 includes an edge 116C, a central portion 116A in which the plurality of needle-like protrusions 110 are arranged, and outer portion 116B which is an area from the central portion 116A to the edge 116C. The shape of the sheet section 116 is defined by the edge 116C in plan view. While the sheet section 116 in FIG. 4 is a rectangle in plan view, the sheet section 116 may be a polygon, a circle, an ellipse, or the like. The sheet section 116 is not limited in shape, as long as the sheet section 116 can include the central portion 116A on which the plurality of needle-like protrusions 110 can be arranged and the outer portion 116B. The transdermal absorption sheet 100 of the present embodiment has a thick portion 116D in the outer portion 116B. The thick portion 116D has a larger thickness in the outer portion 116B of the sheet section 116.

The needle-like protrusions 110 protrude from the sheet section 116, and can be defined by determining a virtual auxiliary face which is in contact with the first principal surface of the sheet section 116.

Next, there will be described a preferable aspect of a mold 13 and a liquid filling device 10 that fills the mold 13 with a liquid medicine which are to be used to perform a liquid medicine filling step in the method of manufacturing a transdermal absorption sheet of the present invention.

Mold

Figure 5A:
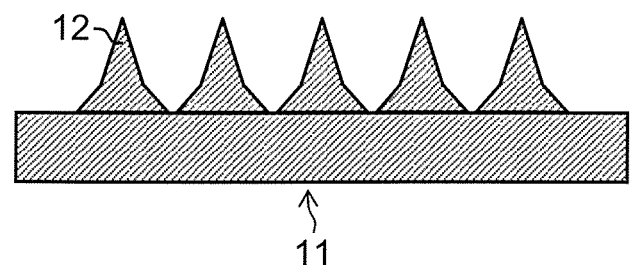
FIGS. 5A to 5C illustrate processes of a method of manufacturing a mold.
Figure 5B:
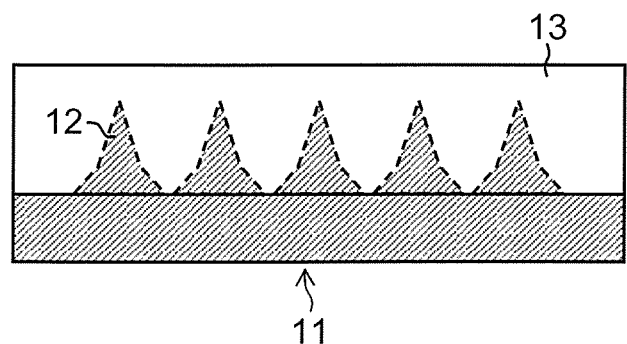
Figure 5C:
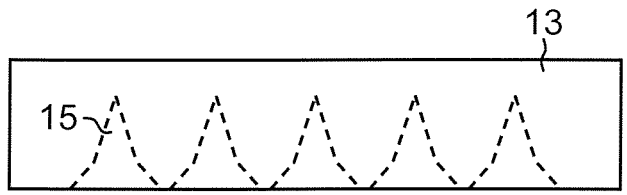

FIGS. 5A to 5C illustrate processes of a method of manufacturing the mold 13.

As illustrated in FIG. 5A, first an original plate is produced which is to be used to produce the mold 13 used for manufacturing a transdermal absorption sheet.

There are two kinds of method of forming an original plate 11. In one of the two kinds of method, a photoresist is applied on a Si base plate, and then the photoresist is exposed and developed. Then, etching such as reactive ion etching (RIE) is applied in order to form, a plurality of protrusions 12 in an array on a surface of the original plate 11, each of the protrusions having a shape identical with the needle-like protrusion 110 of the transdermal absorption sheet. When etching such as RIE is applied to form the protrusions 12 on the surface of the original plate 11, the etching to the Si base plate may be performed from an oblique direction while the Si base plate is rotated.

In the other of the two kinds of method, a metal base plate such as made of stainless steel, aluminum alloy, and Ni, is worked with a cutting tool such as a diamond cutting tool to form a plurality of protrusions 12 in an array on the surface of the original plate 11.

Next, as illustrated in FIG. 5B, the mold 13 is produced by using the original plate 11. The mold 13 is usually produced with a method using Ni electroforming or the like. Since the original plate 11 has the protrusions 12 each formed in the shape of a cone or a quadrangular prismoid (e.g. a quadrangular pyramid) with an acute tip, there are four methods which can accurately transfer the shape of the original plate 11 to the mold 13, release the mold 13 from the original plate 11, and manufacture the mold 13 at low cost.

A first method of forming the mold 13 includes: pouring a silicone resin in which a hardening agent is added into polydimethylsiloxane (PDMS), such as Sylgard 184 of Dow Corning Corp. (Sylgard: registered trademark), to the original plate 11; heating the original plate 11 at 100° C. to cure; and then releasing the mold 13 from the original plate 11. A second method includes: pouring an ultraviolet light curable resin which is curable by irradiation with an ultraviolet light, to the original plate 11; and releasing the mold 13 from the original plate 11 after irradiating the original plate 11 with an ultraviolet light in a nitrogen atmosphere. A third method includes: pouring a solution in which a plastic resin, such as polystyrene and polymethyl methacrylate (PMMA), is dissolved in an organic solvent to the original plate 11 which has been coated with a release agent; and releasing the mold 13 from the original plate 11 after volatizing the organic solvent to cure the solution by drying. A fourth method is to produce a reverse mold by using Ni electroforming.

Accordingly, the mold 13 with two-dimensionally arrayed needle-like recessed portions 15 which have a reversed shape of the protrusions 12 of the original plate 11 is produced. The mold 13 produced in this way is illustrated in FIG. 5C. Since the protrusions 12 of the original plate 11 have the same shape as those of the needle-like protrusions 110 of the transdermal absorption sheet, as illustrated in FIG. 5C, the mold 13 with the plurality of needle-like recessed portions 15, being a reverse mold of the needle-like protrusions 110 of the transdermal absorption sheet, is produced. The mold 13 can be easily produced any number of times by any one of the four methods.

Figure 6:
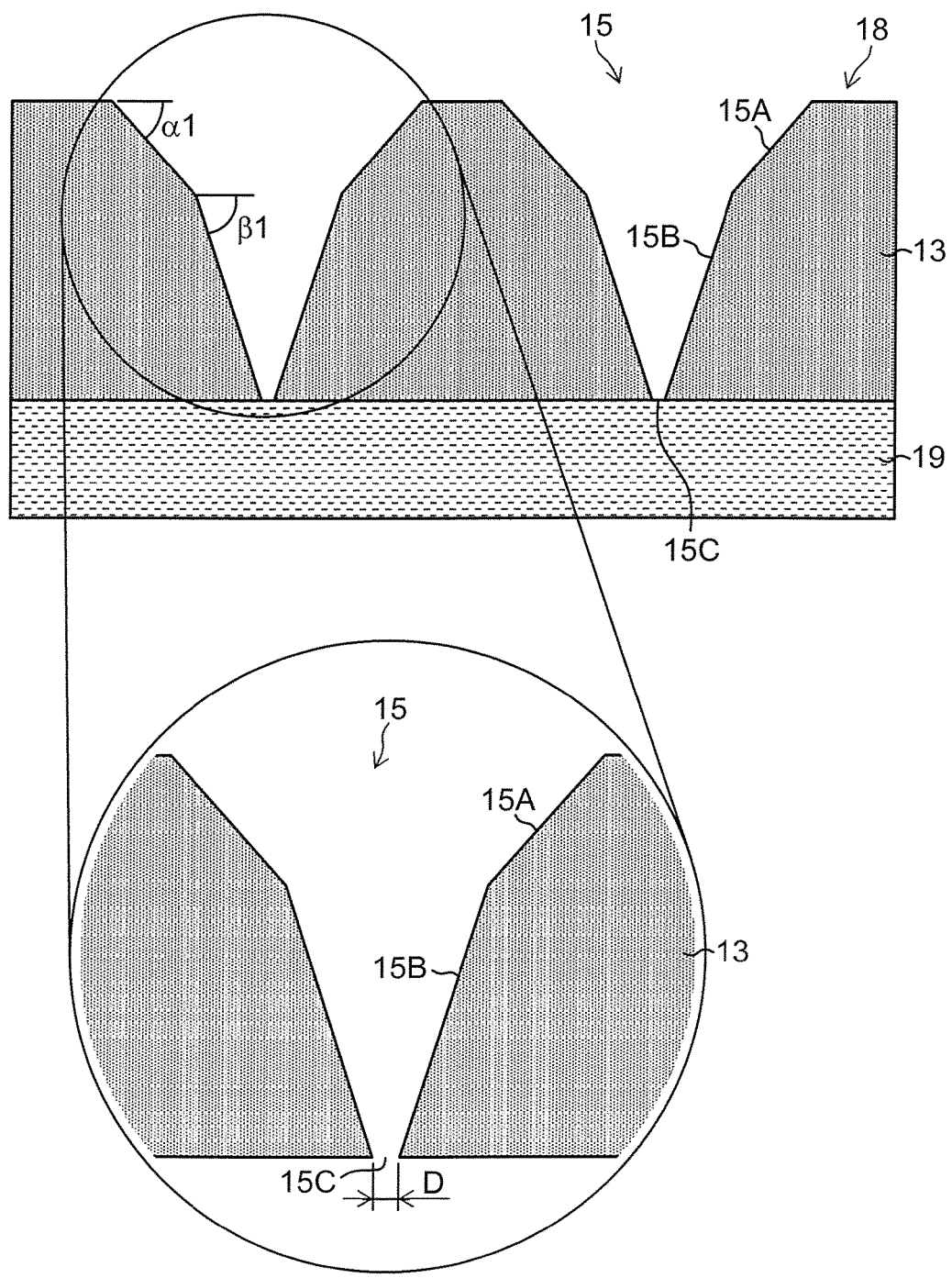
FIG. 6 is a partial enlarged view of a mold composite.

FIG. 6 illustrates an aspect of a mold composite 18 which is more preferable in performing the method of manufacturing a transdermal absorption sheet. As illustrated in FIG. 6, the mold composite 18 includes the mold 13 with the needle-like recessed portions 15 each of which has a tip provided with a through-hole 15C, and a gas-permeable sheet 19 that adheres to the mold 13 on a through-hole 15C side and is made of a material that is permeable to gas and is not permeable to liquid. The through-hole 15C allows the tip of the needle-like recessed portion 15 to communicate with the atmosphere through the gas-permeable sheet 19. The tip of the needle-like recessed portion 15 indicates a side which is tapered in a depth direction of the mold 13, and is opposite to a side filled with the liquid medicine that is a solution containing a medicine and a base material liquid that is a solution containing no medicine.

Using the mold composite 18 as described above enables only an air existing in the needle-like recessed portions 15 to be removed from the needle-like recessed portions 15 through the through-hole 15C without permeation of a transdermal absorption material solution (dissolution) with which the needle-like recessed portions 15 are filled. Thus, transfer properties (transferability) of the shape are improved when the shape of the needle-like recessed portions 15 is transferred to the transdermal absorption material, and thus a sharper needle-like protrusion can be formed.

It is preferable that a diameter D of the through-hole 15C is within a range from 1 μm to 50 μm. This range allows an air to be easily released, and thus enables a tip of the needle-like protrusion 110 of the transdermal absorption sheet to be formed in a sharp shape. As the gas-permeable sheet 19 made of a material that is permeable to gas and is not permeable to liquid, Poreflon (a registered trademark of Sumitomo Electric Hardmetal Corp.) is suitably available, for example.

As described above, the through-hole 15C is provided in the mold 13 to improve a filling property of a liquid medicine 22 and a releasing property of the mold 13, and the present invention is applicable to the liquid filling step regardless of whether there is the through-hole 15C or not.

As a material to be used for the mold 13, an elastic material and a metal material are available. Particularly, an elastic material is preferable, and a material with high gas permeability is more preferable.

Oxygen permeability representing the gas permeability is preferably more than $1\times10^{-12}$ (mL/s·m·Pa), and is more preferably more than $1\times10^{-10}$ (mL/s·m·Pa). Forming the mold 13 of a material with high gas permeability enables a solution containing a medicine to be sucked by sucking from a back surface of the mold 13, and thus filling into the needle-like recessed portion 15 can be accelerated. In addition, an air existing in the needle-like recessed portions 15 of the mold 13 can be removed from the mold 13 side. Thus, a transdermal absorption sheet with less defects can be manufactured.

The material described above is specifically formed by melting general engineering plastic, or by dissolving the general engineering plastic in a solvent, the general engineering plastic including silicone resin (e.g. Sylgard 184 (registered trademark) of Dow Corning Corp., 1310 ST (part number) of Shin-Etsu Chemical Co., Ltd.), ultraviolet light curable resin, polystyrene resin, polymethyl methacrylate (PMMA), epoxy resin, PET resin (polyethylene terephthalate), POM resin (polyoxymethylene), Teflon (registered trademark) resin (polytetrafluoroethylen), PS resin (polystyrene), PE resin (polyethylene), phenol resin, and urethane resin.

Among them, silicone-rubber-based material has durability against transfer by repeated pressurizing as well as a good releasing property from material, and thus it is suitably available.

In addition, the metal material includes Ni, Cu, Cr, Mo, W, Ir, Tr, Fe, Co, MgO, Ti, Zr, Hf, V, Nb, Ta, α-type aluminum oxide, zirconium oxide, stainless steel (Stavax), and their alloys. As a material for a frame 14, a material similar to that of the mold 13 is available.

Medicine

A medicine to be contained in a solution with which the needle-like recessed portions 15 are filled is not limited, and a substance with physiologically activity is available. It is preferable that the medicine is selected from peptide, protein, nucleic acid, polysaccharide, vaccine, a medicinal compound, or a cosmetic ingredient. In addition, it is preferable that the medicinal compound belongs to a water-soluble low-molecular compound. The low-molecular compound has a molecular weight within a range from a few hundreds to a few thousands.

It is preferable to that the water-soluble high-molecular substance to be contained in a layer containing a medicine is a one which has no interaction with a medicine to be contained in the layer. For example, in a case where protein is used as a medicine, mixing a chargeable high-molecular substance into the protein causes the protein and the high-molecular substance to form an aggregate by electrostatic interaction, thereby causing agglomeration and precipitation of the protein. Thus, in a case where a chargeable substance is used as a medicine, it is preferable to use a non-chargeable water-soluble high molecular substance, such as hydroxyethyl starch and dextran.

Liquid Filling Device

Figure 7:
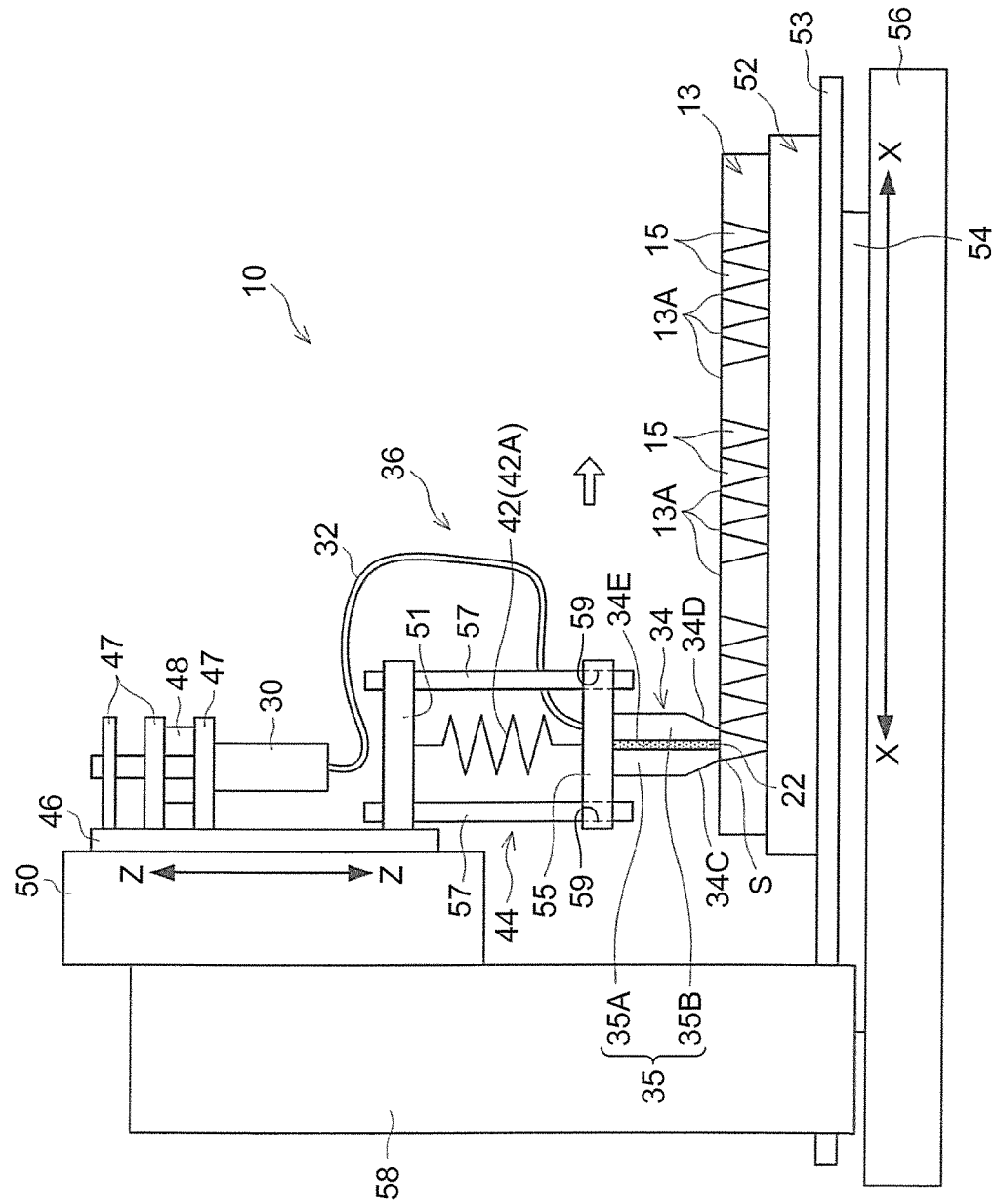
FIG. 7 is a schematic structural view of a liquid filling device using a coil spring as an elastic body.

FIG. 7 is a schematic view illustrating an example of general structure of the liquid filling device 10.

As illustrated in FIG. 7, the liquid filling device 10, as basic structure, includes: a liquid feeder 36 having a feeding liquid tank 30 for storing a liquid medicine and a nozzle 34 attached to the feeding liquid tank 30; a Z-axis drive unit 50 configured to vertically move the liquid feeder 36 up-and-down in a vertical direction (Z-axis direction); a suction base (base) 52 on which the mold 13 is placed and fixed; a load cell 53 that measures a pressing force pressing a nozzle tip of the nozzle on a surface of the mold 13; an X-axis drive unit 54 configured to drive the suction base 52 in an X-axis direction being a movement direction relative to the nozzle 34; a stand 56 that supports the device; and a control system 58 that controls the entire liquid filling device 10.

The feeding liquid tank 30 is disposed in an upper portion of a slider 46 that drives in a vertical direction of the Z-axis drive unit 50, and a discharge device 48 is provided above the feeding liquid tank 30 to pressurize the inside of the feeding liquid tank 30 to supply the liquid medicine 22 to the nozzle 34. The feeding liquid tank 30 and the discharge device 48 are supported by three cantilevered brackets 47 supported by the slider 46.

A slit portion 34E is formed inside the nozzle 34 to communicate with an opening 34B, and a supply port (not illustrated) to the slit portion 34E, and the feeding liquid tank 30, are connected to each other through a pressure-resistant hose 32.

The present embodiment is described in a case where the nozzle 34 moves with respect to the mold 13 fixed by the X-axis drive unit 54. An arrow direction (X-axis direction) in which the nozzle 34 of FIG. 7 moves is referred to as a filling movement direction.

In FIG. 7, while the whole of the liquid feeder 36 including the feeding liquid tank 30 and the nozzle 34 is configured to be driven in the vertical direction by the Z-axis drive unit 50, the feeding liquid tank 30 does not need to be driven in the vertical direction, and thus only the nozzle 34 may be driven by the Z-axis drive unit 50.

Figure 8:
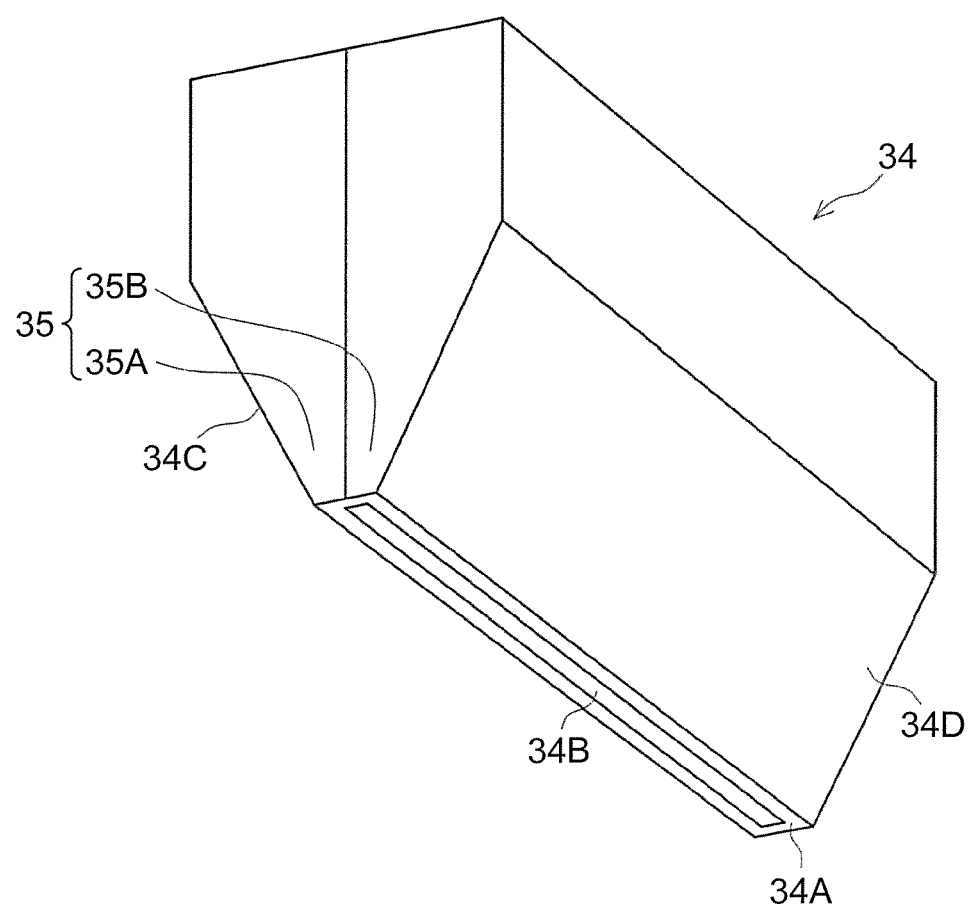
FIG. 8 is a perspective view illustrating structure of a nozzle.

FIG. 8 is a perspective view of an outline of the nozzle 34. As illustrated in FIG. 8, the nozzle 34 includes a nozzle tip 35 composed of a downstream side nozzle tip portion 35A and an upstream side tip portion 35B. The nozzle tip 35 includes a lip face 34A that is a flat face facing the surface of the mold 13, and two inclined faces 34C and 34D that extend outward in a direction away from the lip face 34A. Of the two inclined faces 34C and 34D, the inclined face on a downstream side and the inclined face on an upstream side as viewed from the nozzle movement direction are referred to as a downstream side inclined face 34C and a upstream side inclined face 34D, respectively. The lip face 34A includes an opening 34B in the shape of a slit to discharge the liquid medicine 22. From a viewpoint of relative movement between the nozzle 34 and the needle-like recessed portion 15, the upstream side indicates a side in a direction in which the needle-like recessed portion 15 to be filled and the nozzle 34 are approached, and the downstream side indicates a side in a direction in which the filled needle-like recessed portion 15 and the nozzle 34 are away from each other.

The opening 34B in the shape of a slit enables a plurality of needle-like recessed portions 15 constituting one row to be simultaneously filled with the liquid medicine 22, for example. A length of the opening 34B in a width direction of the nozzle and a width (a gap of the opening) of the opening 34B are appropriately determined depending on the number of the needle-like recessed portions 15 to be simultaneously filled.

Increasing the opening 34B in length enables more needle-like recessed portions 15 to be simultaneously filled with the liquid medicine 22. Accordingly, productivity can be improved.

As a material to be used for the nozzle 34, an elastic material and a metal material are available. The material, for example, includes Teflon (registered trademark), polyacetal, polyethylene, stainless steel (SUS), and titanium. It is preferable to apply a water-repellent coating or a nonadherent coating to the surface of the nozzle to reduce a stain caused by the liquid medicine adhering to the nozzle. Particularly, it is preferable to apply a water-repellent coating or a nonadherent coating to the downstream side inclined face 34C of the downstream side nozzle tip portion 35A to prevent the liquid medicine from wetting up (wetting spread) during filling.

It is also preferable to apply a hydrophilic coating to an internal wall face of the slit portion 34E to allow the liquid medicine 22 to uniformly spread in the width direction of the nozzle during filling.

To allow the nozzle 34 to fill the needle-like recessed portions 15 of the mold 13 with the liquid medicine 22, the nozzle 34 is brought close to the mold 13 by using the Z-axis drive unit 50 to reach a Z-coordinate at which a pressing force applied on the surface of the mold 13 by the nozzle 34 becomes a desired pressing force. Then, whether the desired pressing force is achieved is checked with the load cell 53.

Subsequently, while the nozzle 34 in contact with the mold 13 is swept in the arrow direction by using the X-axis drive unit 54, the liquid medicine 22 is discharged from the opening 34B when the nozzle tip 35 of the nozzle 34 is positioned above the needle-like recessed portion 15. This allows the nozzle 34 to fill the needle-like recessed portion 15 of the mold 13 with the liquid medicine 22. This case includes both an aspect in which the needle-like recessed portion 15 is filled with the liquid medicine 22 while the nozzle 34 is continuously moved, and an aspect of intermittent movement in which the nozzle 34 is temporarily stopped above the needle-like recessed portion 15 to fill it with the liquid medicine 22 during movement of the nozzle 34 and the nozzle 34 is moved again after the filling. Both of the aspects have a state where the nozzle tip 35 of the nozzle 34 is in contact with the surface of the mold 13.

In the liquid filling device 10 to be used in the method of manufacturing a transdermal absorption sheet of the present invention, the nozzle 34 is supported through an elastic body 42 by the Z-axis drive unit 50 configured to vertically move the nozzle 34, along with the basic structure described above. This allows the elastic body 42 to absorb variation in pressing force by the nozzle 34 against the surface of the mold 13.

As the elastic body 42, there is available any kind of elastic body that has restoring capacity which allows to deform when force is applied to the elastic body and to restore to an original shape when the force is removed. Particularly, it is preferable to use an elastic body having elastic force against translational movement in a thickness direction of the mold 13, and an elastic body having both an elastic force against the translational movement in the thickness direction of the mold 13 and an elastic force against in-plane rotation (mainly rotation in a horizontal plane) including a direction of relative movement between the nozzle 34 and the mold 13.

As the elastic body 42 having an elastic force against the translational movement in the thickness direction of the mold 13, other than a coil spring 42A, an extension spring, a disk spring, a resin having an elastic force, an air spring, and an elastic body 42 being a combination of them may also be used.

As the elastic body 42 having both the elastic force against the translational movement in the thickness direction of the mold 13 and the elastic force against the in-plane rotation including the direction of the relative movement between the nozzle 34 and the mold 13, other than a leaf spring 42B, a torsion spring, a resin spring, and an elastic body 42 being a combination of them may also be used.

Regardless of the elastic force described above, because any force functions as a restoring force in a direction opposite to deviation (increase or decrease) in the displacement amount by pressing of the mold 13 can work in a manner similar to the elastic force of the elastic body described above, oscillation of a pendulum using gravity, buoyant force, or the like may be used.

The elastic body 42 needs to absorb variation in pressing force by the nozzle 34 against the surface of the mold 13 to eliminate variation in the displacement amount by pressing of the needle-like recessed portion 15 of the mold 13. Thus, it is preferable that the elastic body 42 is made of a material softer than that of the mold 13, or a total of elastic constants (a spring constant in the case of a spring) of respective elastic bodies 42 provided between the Z-axis drive unit 50 and the nozzle 34 is less than hardness or an elastic constant of the mold 13.

However, if the elastic body 42 has an elastic constant (a spring constant in the case where the elastic body is a spring) reduced (softened) in a direction of pressing by the nozzle, elastic constants tend to be softened also in the width direction of the nozzle 34 and in the filling movement direction thereof. In this case, when the nozzle 34 is pressed against the mold 13, the nozzle 34 tends to be easily rotated in a horizontal surface by the elastic body 42, and the nozzle 34 tends to easily have extra variation components in the width direction of the nozzle 34 and the filling movement direction thereof. These are unfavorable factor for filling accuracy in filling the needle-like recessed portions 15 with the liquid medicine 22.

As a countermeasure against the above, it is preferable to further provide a guide mechanism 44 for regulating a movable range of the nozzle 34 in a movement direction.

In this case, combining the elastic body 42 that provides the elastic force against the translational movement in the thickness direction of the mold, such as the coil spring 42A, with the guide mechanism 44 enables to prevent the unfavorable factor described above to be prevented from occurring, and enables to configure a nozzle holding section in a space-saving manner.

In a case where the elastic body 42 having both the elastic force against the translational movement in the thickness direction of the mold and the elastic force against the in-plane rotation is used, such as the leaf spring 42B, the unfavorable factor described above can be prevented, and thus the guide mechanism 44 does not need to be provided.

Meanwhile, since the elastic body 42 having elastic force only in the thickness direction of the mold 13, such as the coil spring 42A, makes translational movement in the thickness direction of the mold 13, the nozzle 34 does not change its posture. As a result, the elastic body 42 has less effect on a geometric relationship between the mold 13 and the nozzle 34, and has an advantage when measuring instruments and auxiliary equipment for filling and filling-related are attached to a nozzle side.

Thus, it is preferable to appropriately determine whether to use the elastic body 42 having elastic force against the translational movement in the thickness direction of the mold 13, or the elastic body 42 having both the elastic force against the translational movement in the thickness direction of the mold and the elastic force against the in-plane rotation. Although the embodiments in which the elastic body 42 is directly or indirectly connected to the nozzle 34 are explained above, the position where the elastic body 42 is provided is not limited to the embodiments. For example, even when the elastic body 42 may be provided in the suction base (base) 52, the similar advantageous effects can be achieved.

The liquid filling device 10 of FIG. 7 shows a case where the coil spring 42A is used as the elastic body 42, and the guide mechanism 44 that guides vertical movement of the nozzle 34 is further provided.

That is, a cantilevered upper plate 51 in the shape of a quadrangle, supported horizontally by the slider 46, is provided in a lower portion of the slider 46, and an upper end of the coil spring 42A is fixed to a lower face of the upper plate 51. Then a lower end of the coil spring 42A is fixed to a lower plate 55 in the shape of a quadrangle, fixed to a horizontal top face of the nozzle 34. Thus, the nozzle 34 is suspended from the upper plate 51 that is vertically moved by the Z-axis drive unit 50, through the coil spring 42A and the lower plate 55.

In a case where the coil spring 42A is provided between the Z-axis drive unit 50 and the nozzle 34, the nozzle 34 cannot be fixed to the Z-axis drive unit 50 in an uniform posture by only the coil spring 42A, and thus the nozzle 34 may have a posture inclined or displaced in all directions other than a pressing direction. As a result, a pressing angle at which the nozzle 34 presses the surface of the mold 13 varies so as to vary a volume of each of the needle-like recessed portions 15, whereby a filling amount of each of the needle-like recessed portions 15 may vary. Thus, it is preferable that the guide mechanism 44 is further provided in a case where the coil spring 42A is used as the elastic body 42.

The guide mechanism 44 is configured such that four guide bars 57 whose upper portions are inserted and fixed to four respective holes drilled at four corners of the upper plate 51, and whose lower end portion are inserted and not-fixed to four respective holes 59 drilled at four corners of the lower plate 55. In this case, the four guide bars 57 are disposed so as to be parallel to a direction of the vertical movement of the nozzle 34, or a pressing direction of the nozzle 34. Accordingly, the guide mechanism 44 allows the nozzle 34 to vertically move only in the pressing direction. Thus, even if the coil spring 42A is used as the elastic body 42, the pressing angle of the nozzle 34 to the mold 13 can be made constant.

As described above, since the nozzle 34 is held by the Z-axis drive unit 50 configured to vertically move the nozzle 34 through the coil spring 42A, the coil spring 42A shrinks in the direction opposite to the pressing direction depending on a level (magnitude) of reaction force when the reaction force in a direction opposite to the pressing direction is applied to the nozzle 34. Accordingly, the coil spring 42A absorbs variation in the pressing force that varies due to factors, such as displacement amount by pressing caused by the nozzle tip 35 of the nozzle 34 pressing the surface of the mold 13, and variation in thickness of the mold. As a result, the volume of each of the arrayed needle-like recessed portions 15 tends to hardly vary, and thus the filling amount of each of the needle-like recessed portions 15 tends to have little variation. In addition, when the coil spring 42A is used as the elastic body 42, it is preferable to provide the guide mechanism 44 that guides the vertical movement of the nozzle 34. Accordingly, the pressing angle is fixed, and thus variation in pressing force due to variation in the pressing angle is also eliminated.

In addition, since the coil spring 42A absorbs variation in pressing force applied to the mold 13, it is prevented that a large liquid pressure is partially applied to a contact portion S (refer to FIGS. 7 and 12) at which the nozzle tip 35 is brought into pressed contact with the surface of the mold 13. Accordingly, it is possible to solve the conventional problem that the liquid medicine 22 leaks to the outside from the contact portion S to which large liquid pressure is applied, and thus the liquid medicine 22 including an expensive medicine is prevented from easily adhering to flat surface portions 13A of the mold 13 other than the needle-like recessed portions 15 of the mold 13 even when filling at high speed.

Figure 9:
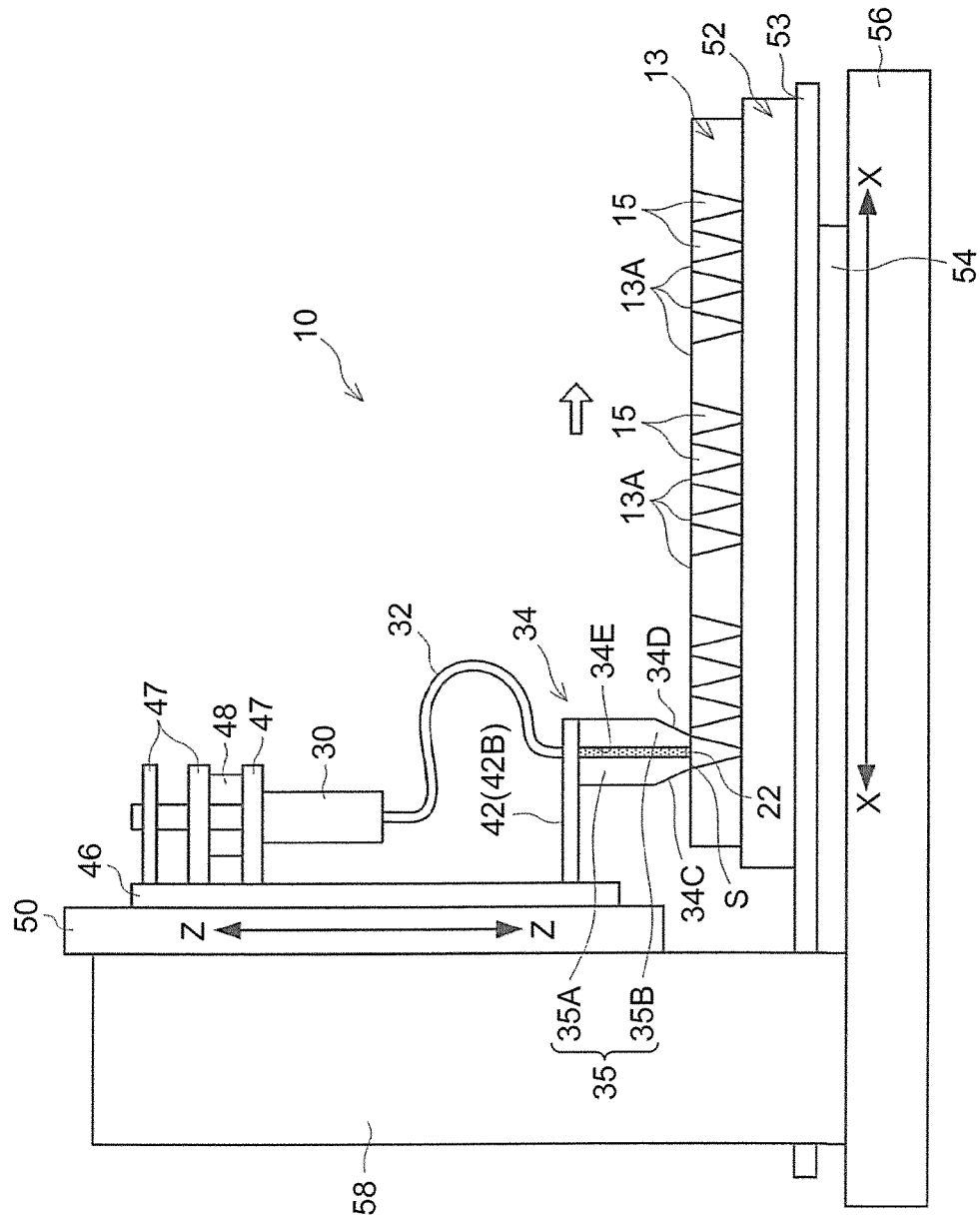
FIG. 9 is a schematic structural view of a liquid filling device using a leaf spring as an elastic body.

The liquid filling device 10 of FIG. 9 shows a case where the leaf spring 42B is used as the elastic body 42. The same member as that described in FIG. 7 is designated by the same reference numeral while description on the member is not duplicated.

As illustrated in FIG. 9, a cantilevered leaf spring 42B in the shape of a quadrangle, supported horizontally by the slider 46, is provided in a lower portion of the slider 46 that is driven in the vertical direction by the Z-axis drive unit 50. Then, the top face of the nozzle 34 is fixed to a lower face of a leading end portion (a filling movement direction side) of the leaf spring 42B.

As described above, when the leaf spring 42B is used as the elastic body 42, the leaf spring 42B wraps depending on a level (magnitude) of reaction force when the reaction force in the direction opposite to the pressing direction is applied to the nozzle 34. Accordingly, the leaf spring 42B absorbs variation in the pressing force that varies due to displacement amount by pressing by the nozzle tip 35 of the nozzle 34 on the surface of the mold 13, variation in thickness of the mold, and the pressing angle. As a result, the volume of each of the arrayed needle-like recessed portions 15 tends to hardly vary, and thus the filling amount of each of the needle-like recessed portions 15 tends to have little variation.

This enables to improve the filling accuracy of the liquid medicine 22 for each of the arrayed needle-like recessed portions 15, as well as enables the liquid medicine 22 including an expensive medicine to be effectively prevented from adhering to the flat surface portions 13A of the mold 13 even when filling at high speed.

Particularly, when the leaf spring 42B is used as the elastic body 42, the nozzle 34 can be fixed to the Z-axis drive unit 50 by using only the elastic body 42. Accordingly, the guide mechanism 44 that typically has a sliding portion is unnecessary, and thus there is no possibility that dust generation (dust generated by friction between the guide bar 57 and the hole 59 in the lower plate 55 in FIG. 7) is induced to mix dust into the needle-like recessed portions 15.

While it is preferable that an elastic constant (a spring constant in the case where the elastic body is a spring) of the elastic body 42 is less than that of the mold 13, too small elastic constant may cause the nozzle 34 to vibrate if there is a steep change in thickness in a portion other than the needle-like recessed portion 15, whereby the mold 13 may be damaged or unfavorable liquid leakage may occur from the nozzle 34. The steep change in thickness includes a level difference formed when a plurality of molds 13 is joined by an adhesive, fusing, or the like, and a level difference caused by a foreign material that is mixed to the mold 13 and adheres thereto.

To avoid the problem of this kind of vibration, it is preferable to provide a viscous substance (not illustrated) between the Z-axis drive unit 50 configured to vertically move the nozzle 34 and the nozzle 34. At that time, it is further preferable to provide the viscous substance in parallel to the elastic body 42, because vibration can be easily attenuated as compared with a case where the viscous substance is provided in series with the elastic body 42.

As the viscous substance, for example, a shock absorber including a rubber bag filled with liquid or gas, a high molecular material with viscous force, or the like, can be suitably applied.

As described above, a viscous substance, which is provided between the Z-axis drive unit 50 configured to vertically move the nozzle 34 and the nozzle 34, enables improve resistance to variation in pressing force of the nozzle 34, even if there is a level difference of joining or a level difference of a foreign material.

As a result, a nozzle position tends to hardly change against a steep change in thickness, and attenuation of vibration caused by the change in thickness increases, whereby the filling accuracy can be further improved.

Next, a method of manufacturing a transdermal absorption sheet of the present embodiment will be described.

Method of Manufacturing Transdermal Absorption Sheet

Figure 10:
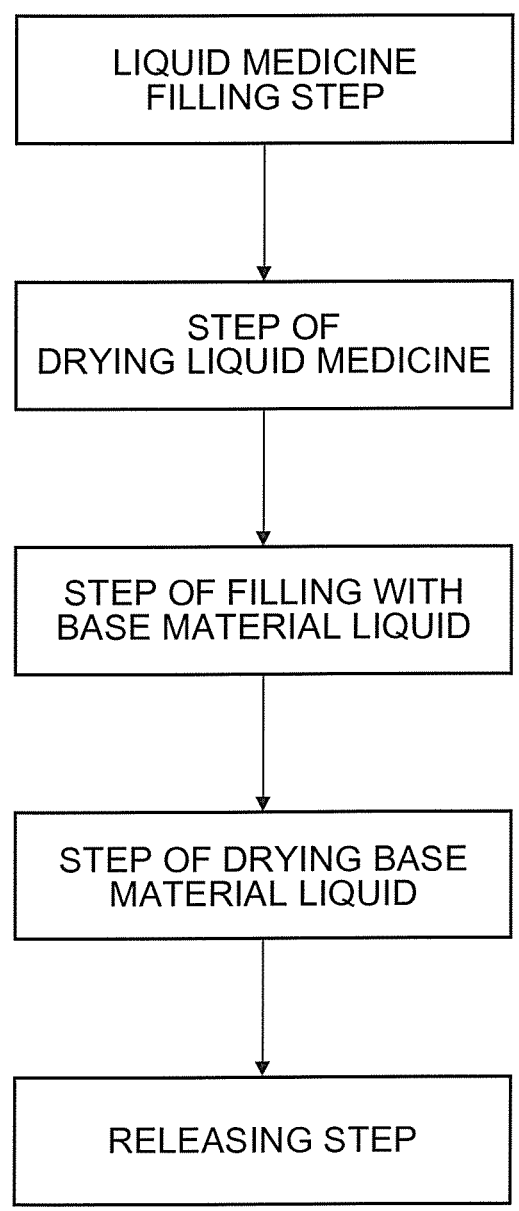
FIG. 10 is a flow chart of a method of manufacturing a transdermal absorption sheet.

The method of manufacturing a transdermal absorption sheet of the present embodiment includes at least five steps of: a liquid medicine filling step; a liquid medicine drying step; a base material liquid filling step; a base material liquid drying step; and releasing step, as illustrated in FIG. 10, the five steps being performed in the order above after a step of preparing the mold 13 and the liquid filling device 10 is performed.

Liquid Medicine Filling Step

Figure 11A:
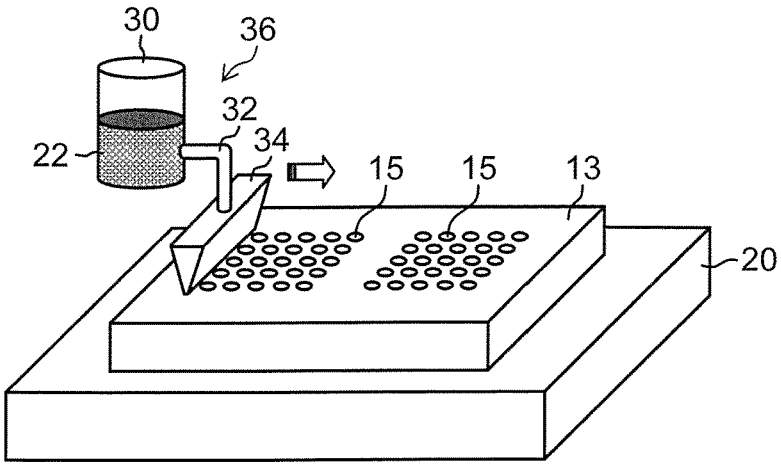
FIGS. 11A to 11C are schematic views illustrating a step of filling needle-like recessed portions of the mold with a liquid medicine.
Figure 11B:
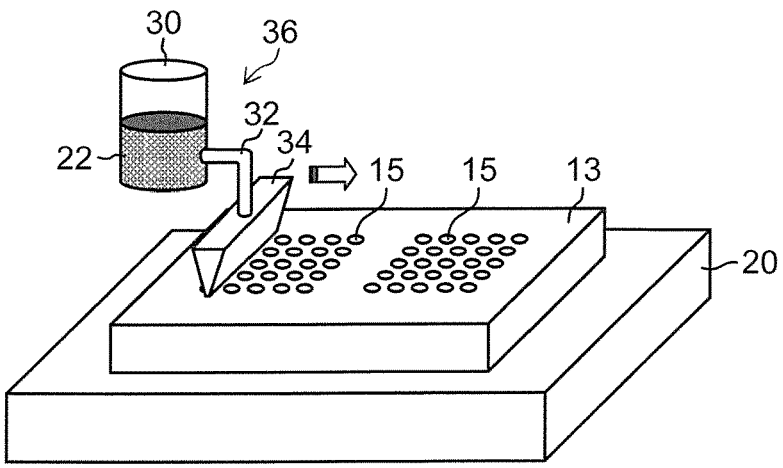
Figure 11C:
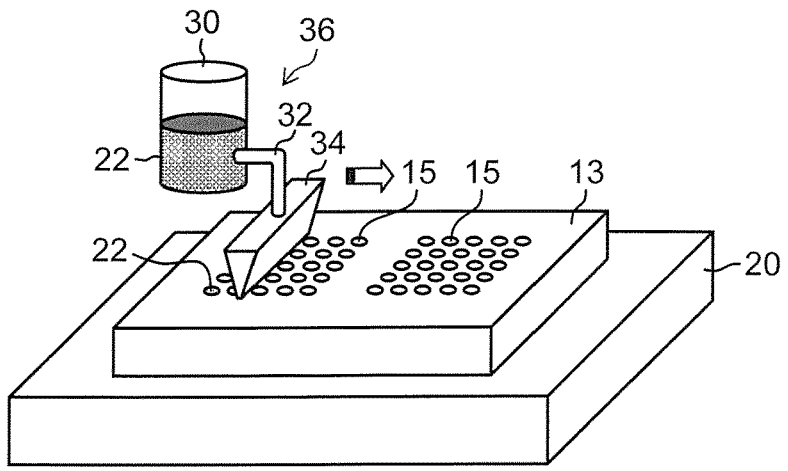

FIGS. 11A to 11C illustrate a basic method of filling the arrayed needle-like recessed portions 15 with the liquid medicine 22 by repeating the following: a filling operation in which the liquid medicine 22 is supplied to the mold 13 from the liquid feeder 36 and one or more needle-like recessed portions 15 are filled with the liquid medicine 22 while the nozzle tip 35 of the nozzle 34 adjusted to a position above the needle-like recessed portions 15 is brought into pressed contact with a surface of the mold; and a moving operation in which the nozzle 34 is relatively moved to the mold 13 while the nozzle tip 35 and the surface of the mold 13 are in contact with each other.

Thus, FIGS. 11A to 11C do not illustrate each of the improvements such as the elastic body 42 (e.g. a coil spring, and a leaf spring), and the guide mechanism 44, which are described in the explanation about the liquid filling device 10.

As illustrated in FIG. 11A, the mold 13 with the arrayed needle-like recessed portions 15 is disposed on a base 20. The mold 13 is provided with two pairs of a plurality of needle-like recessed portions 15 having an array of 5 by 5 portions. There is prepared the liquid feeder 36 having the feeding liquid tank 30 for storing the liquid medicine 22, the pressure-resistant hose 32 connected to the feeding liquid tank 30, and the nozzle 34 connected to a leading end of the pressure-resistant hose 32. The liquid medicine 22 is discharged from the tip of the nozzle 34.

Subsequently, the filling operation will be described with reference to FIG. 11B. As illustrated in FIG. 11B, the opening 34B of the nozzle 34 is adjusted to a position above the needle-like recessed portions 15. Since the nozzle 34 for discharging the liquid medicine 22 is pressed on the mold 13, the lip face 34A of the nozzle 34 and the surface of the mold 13 are in contact with each other. The liquid feeder 36 supplies the liquid medicine 22 to the mold 13, and the needle-like recessed portions 15 are filled with the liquid medicine 22 discharged from the opening 34B of the nozzle 34. In the present embodiment, a plurality of needle-like recessed portions 15 constituting one row is simultaneously filled with the liquid medicine 22. However, a filling manner is not limited to the above manner, and the needle-like recessed portions 15 can be filled one by one.

In a case where the mold 13 is formed of a material with gas permeability, the liquid medicine 22 can be sucked by sucking from a back surface of the mold 13, and thus filling into the needle-like recessed portion 15 can be accelerated.

Subsequently to the filling operation of FIG. 11B, as illustrated in FIG. 11C, the liquid feeder 36 is relatively swept in the filling movement direction of the opening 34B while the nozzle tip of the nozzle 34 and the surface of the mold 13 are in contact with each other. The nozzle 34 is swept on the mold 13 and moved to the needle-like recessed portions 15 with which no liquid medicine 22 is filled. Then, the opening 34B of the nozzle 34 is adjusted to a position above the needle-like recessed portions 15. In the present embodiment, while an example of sweeping the nozzle 34 is described, the mold 13 may be swept.

Repeating filling operation of FIG. 11B and moving operation of FIG. 11C allows the needle-like recessed portions 15 arranged to form an array of 5 by 5 portions to be filled with the liquid medicine 22. Once the needle-like recessed portions 15 arranged to form the array of 5 by 5 portions is filled with the liquid medicine 22, the liquid feeder 36 is moved to the adjacent needle-like recessed portions 15 arranged to form an array of 5 by 5 portions, and then the filling operation of FIG. 11B and the moving operation of FIG. 11C are repeated. The adjacent needle-like recessed portions 15 arranged to form the array of 5 by 5 portions are also filled with the liquid medicine 22.

When filling the needle-like recessed portions 15 with the liquid medicine 22 is completed and the nozzle 34 is raised from the surface of the mold 13, it is preferable to suck the liquid medicine 22 adhering to the nozzle tip 35 by setting the feeding liquid tank 30 or the nozzle 34 to negative pressure to the atmospheric pressure. This enables the liquid medicine to be further prevented from adhering to flat surface portions other than the needle-like recessed portions 15, as well as enables a liquid level in subsequent filling to be uniform, whereby filling accuracy can be improved.

In the liquid medicine filling step, it is possible to use the mold composite 18 illustrated in FIG. 6 so that the liquid medicine 22 is sucked from the through-hole 15C side to fill the needle-like recessed portions 15 with the liquid medicine 22. Particularly, bubbles taken in the liquid medicine 22 are unfavorable, because medicine content varies.

Figure 13:
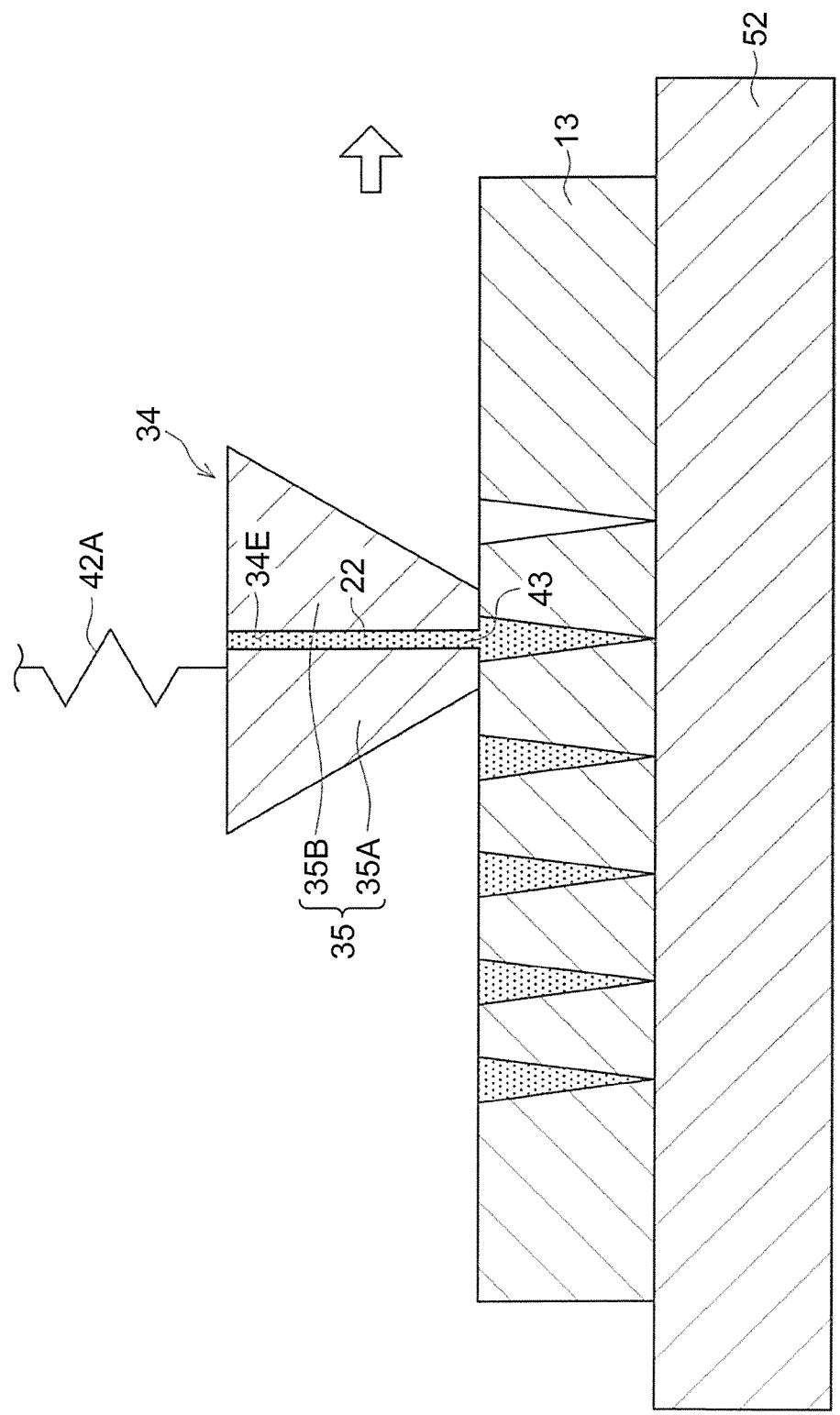
FIG. 13 illustrates a relationship between the nozzle and the mold in moving operation in the liquid filling step.

The filling operation of FIG. 12 and the moving operation of FIG. 13 are illustrated to describe operation of the elastic body 42.

As illustrated in FIGS. 12 and 13, the nozzle 34 is held by the Z-axis drive unit 50 configured to vertically move the nozzle 34 through the elastic body 42 in order to press the nozzle tip 35 against the surface of the mold 13 and bring the nozzle tip 35 into contact with the surface of the mold 13. The elastic body 42 is configured to absorb the variation in pressing force by the nozzle 34 to the surface of the mold 13. That is, since the nozzle 34 is held by the Z-axis drive unit 50 configured to vertically move the nozzle 34 with the elastic body 42 interposed between them, a transdermal absorption sheet is manufactured while the elastic body 42 absorbs variation in pressing force to the mold 13 when the nozzle tip 35 is pressed and to be brought into contact with the surface of the mold 13. FIGS. 12 and 13 each are an illustration in which the coil spring 42A is used as the elastic body 42.

Accordingly, the elastic body 42 absorbs variation in displacement amount by pressing the nozzle tip 35 on the surface of the mold 13; variation in thickness of the mold 13; and variation in pressing force of the nozzle 34 caused by a pressing angle and so on so as to make the pressing force uniform (constant). As a result, the filling accuracy of the liquid medicine 22 for each of the arrayed needle-like recessed portions 15 can be improved.

Figure 14A:
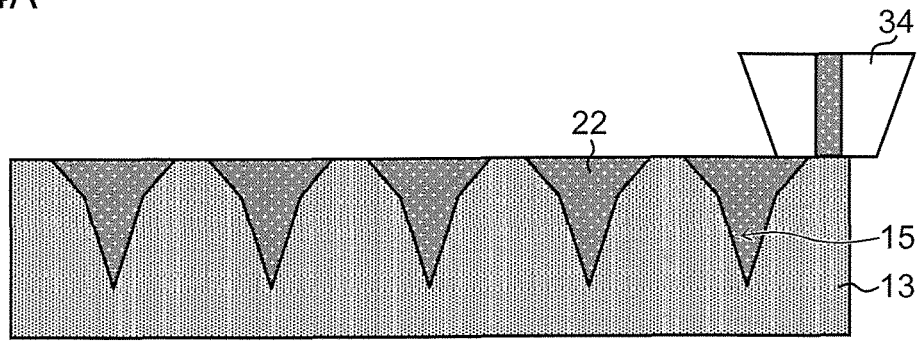
FIGS. 14A to 14D illustrate steps from a step of drying the liquid medicine to a step of drying a base material liquid.
Figure 14B:
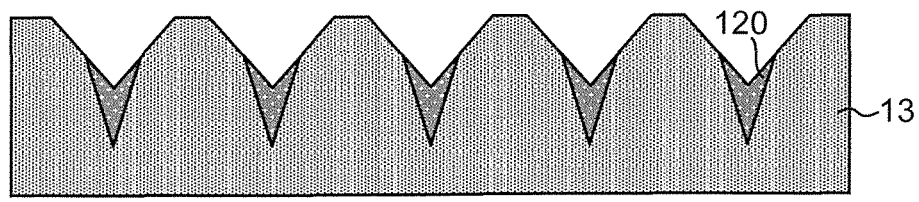
Figure 14C:
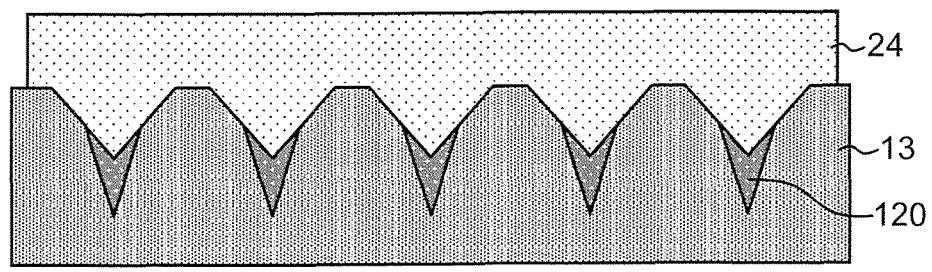
Figure 14D:
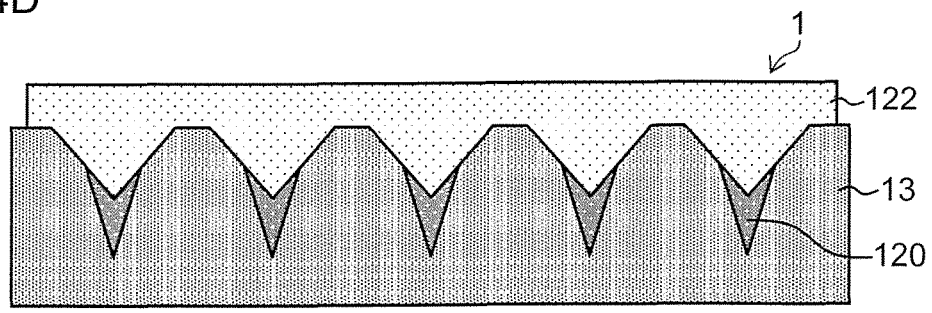
Figure 15:
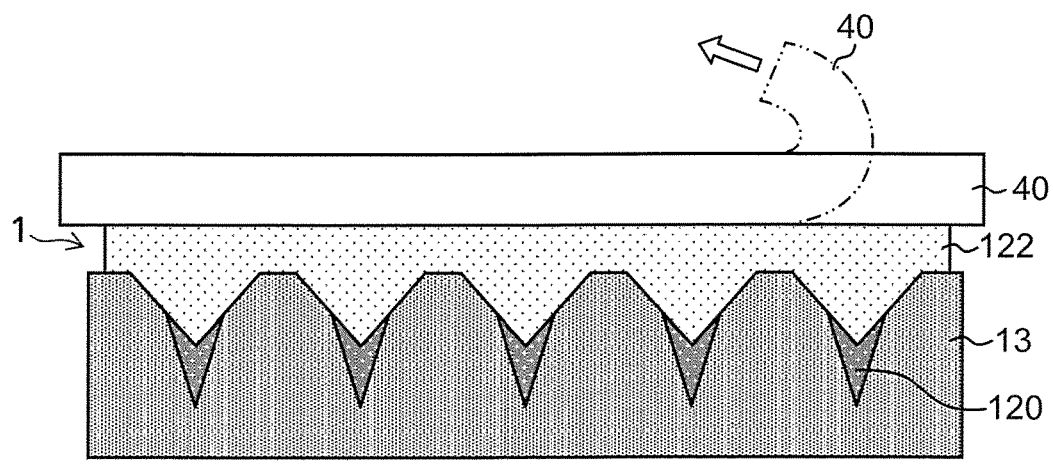
FIG. 15 illustrates a releasing step.
Figure 16:
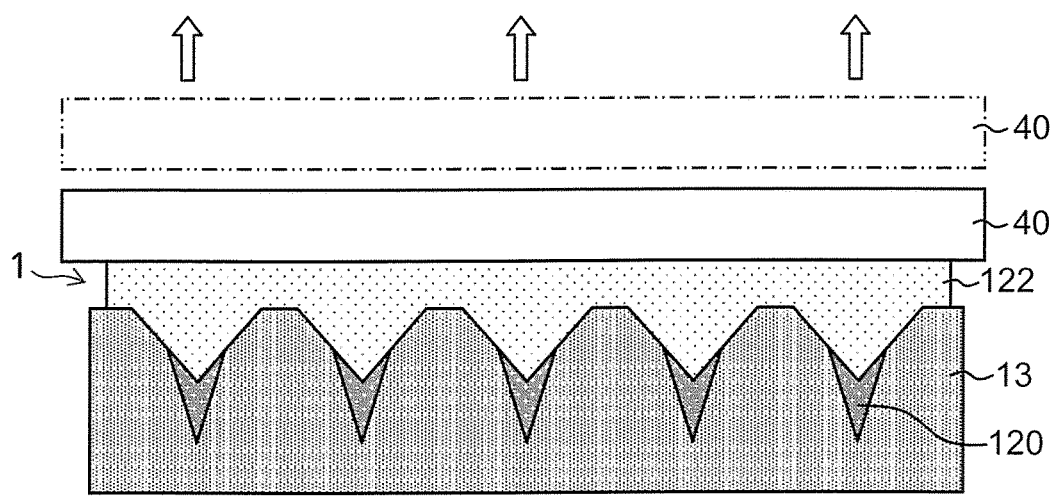
FIG. 16 illustrates another releasing step.

Once the liquid medicine filling step illustrated in FIG. 14A is completed, a liquid medicine drying step and a second and subsequent layer filling step are repeatedly performed as needed depending on a needle shape to be formed, and then processing proceeds to a releasing step. For example, as illustrated in FIGS. 14B to 14D, there are performed steps of: a liquid medicine drying step for drying and solidifying the liquid medicine 22 to form the first layer 120 containing the medicine in the needle-like recessed portion 15; a base material filling step for applying a base material liquid 24 containing no medicine on the first layer 120 containing the medicine to fill the needle-like recessed portion 15 with the base material liquid 24; and drying step for drying and solidifying the base material liquid 24 to form a second layer 122. Then, the processing proceeds to a releasing step illustrated in FIG. 15 or FIG. 16. Reference numeral 40 in FIG. 15 or FIG. 16 designates a sheet-like releasing base material that includes an adhesive layer and is used to release the manufactured transdermal absorption sheet from the mold 13.

Hereinafter, the present invention will be more specifically described by using examples of the present invention. While there will be shown a material, an amount used, a ratio, processing contents, a processing procedure, and the like in the examples, they can be appropriately changed without departing from the spirit of the present invention. Thus, the scope of the present invention should not be limitedly interpreted according to the specific examples shown below.

EXAMPLES

Test A

A test A is performed to compare filling accuracy of a case (Example 1) where the needle-like recessed portions 15 of the mold 13 is filled with the liquid medicine 22 by using the liquid filling device 10 in which the nozzle 34 is held by the Z-axis drive unit 50 through the elastic body 42, with that of a case (Comparative Example 1) where the needle-like recessed portions 15 of the mold 13 is filled with the liquid medicine 22 by using a liquid filling device in which the nozzle 34 is directly fixed to the Z-axis drive unit 50 not through the elastic body 42.

The filling accuracy was compared by checking variation in filling amount of the liquid medicine 22 which is filled in the needle-like recessed portions 15 between a case where the liquid filling device 10 of Example 1 is used to fill the mold 13 formed by a method described below with the liquid medicine 22, and a case where the liquid filling device of Comparative Example 1 is used to fill the mold 13 with the liquid medicine 22.

The variation in the filling amount was checked by repeating the filling operation five times.

The mold 13, a preparation of each of the liquid medicine 22 and the base material liquid 24, structure of the liquid filling device of each of Example 1 and Comparative Example 1, filling and drying of the liquid medicine 22, coating and drying of the base material liquid 24, and releasing of a polymer sheet 1, used in the test A, are as follows.

Mold

Figure 17B:
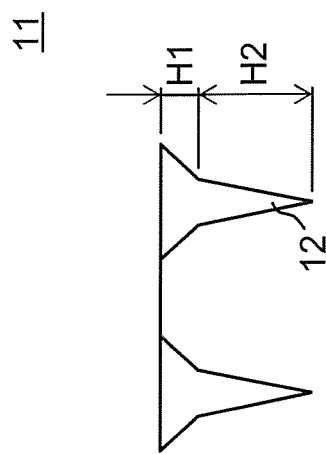
FIGS. 17A and 17B are a plan view of an original plate and a side view of recessed portions of the original plate.
Figure 17A:
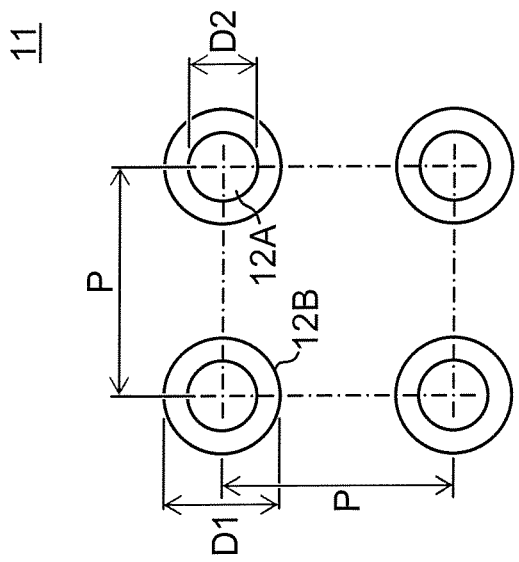

The original plate 11 was produced by forming the protrusions 12 each with a needle-like structure in which a cone 12A having a bottom face with a diameter D2 of 300 μm and a height H2 of 500 μm is formed on a truncated cone 12B having a lower bottom face with a diameter D1 of 500 μm and a height H1 of 150 μm, as illustrated in FIGS. 17A and 17B, on a surface of a flat Ni plate having a size of 40 mm on each side, the protrusions 12 being formed by grinding to form a two-dimensional array of 10 rows by 10 lines at a pitch P of 1000 μm.

On the original plate 11, a film with a thickness of 0.6 mm was formed of silicone rubber (SILASTIC-MDX4-4210 of Dow Corning Corp.), and was thermally cured while a tip of the cone of the original plate 11 was allowed to protrude by 50 μm from a face of the film, and then the film was released. Accordingly, a reverse mold of the silicone rubber having a through-hole with a diameter of about 30 μm was formed.

A plane having a size of 30 mm on each side in which an array of 10 rows by 10 lines of the needle-like recessed portions was formed in its central portion was cut off from the reverse mold of the silicone rubber, and was used as the mold 13. A surface of the mold 13 having a wider opening of the needle-like recessed portion 15 was treated as a front surface, and a surface of the mold 13 having the through-hole (air release hole) with a diameter of 30 μm was treated as a back surface.

Preparation of Liquid Medicine

A polymer solution containing a medicine, or the liquid medicine 22, was formed by adding 2 mass % human serum albumin (made of Wako Pure Chemical Industries, Ltd.) into an aqueous solution containing 8% hydroxyethyl starch (made of Fresenius SE & Co. KGaA) prepared by dissolving the hydroxyethyl starch in water. After the preparation, the liquid medicine 22 was exposed under a reduced pressure of 3 kPa for four minutes to be sufficiently degassed.

Preparation of Base Material Liquid

A polymer solution not-containing a medicine, or the base material liquid, was an aqueous solution containing 40% chondroitin sulfuric acid (made of Maruha Nichiro Corp.) prepared by dissolving the chondroitin sulfuric acid in water. After the preparation, the base material liquid was exposed under a reduced pressure of 3 kPa for four minutes to be sufficiently degassed.

Liquid Filling Device

The liquid filling device basically included the X-axis drive unit 54 for controlling coordinates of relative positions of the mold 13 and the nozzle 34 in the filling movement direction (X-axis direction), the Z-axis drive unit 50 for vertically moving the nozzle 34 relative to the surface of the mold 13, the liquid feeder 36 (high precision microdetermination dispenser SMP-3 made of Musashi Engineering Inc.) capable of attaching the nozzle 34, the suction base 52 for fixing the mold 13, and the load cell 53 (LCX-A-500N made of Kyowa Electronic Instruments Co., Ltd.) for measuring pressing force of the nozzle 34.

In Example 1, the nozzle 34 was held by the Z-axis drive unit 50 through the leaf spring 42B serving as the elastic body 42, and in Comparative Example 1, the Z-axis drive unit 50 and the nozzle 34 were directly fixed to each other without providing the elastic body 42.

In Example 1, the leaf spring 42B, as the elastic body 42, having a thickness of 200 μm and a width of 3 cm was disposed at the center position in a width direction of the nozzle, and the nozzle 34 is fixed to the leaf spring 42B so that the Z-axis drive unit 50 and the nozzle 34 were away from each other by 5 mm.

In both Example 1 and Comparative Example 1, the gas-permeable sheet 19 (Poreflon FP-010 made of Sumitomo Electric Hardmetal Corp.) having a size of 15 mm on each side was placed on the horizontal suction base 52, and the mold 13 was placed on the gas-permeable sheet 19 so that the front surface of the mold 13 was upward. Then, the gas-permeable sheet 19 and the mold 13 were sucked and fixed to the suction base 52 by depressurizing at a suction pressure with a gauge pressure of 90 kPa from a back surface side of the mold 13.

The nozzle 34 having basic structure as illustrated in FIG. 8 was used. The nozzle 34 was made of stainless steel (SUS). The slit-like opening 34B with a length of 12 mm and a width of 0.2 mm was formed in a middle of the lip face 34A with a length of 20 mm and a width of 2 mm. The nozzle 34 was connected to the feeding liquid tank 30 through the pressure-resistant hose 32.

Method of Filling with Liquid Medicine and Method of Drying Liquid Medicine

In both Example 1 and Comparative Example 1, 3 mL of the liquid medicine 22 containing a medicine was fed into the feeding liquid tank 30 and the nozzle 34. Then, the nozzle 34 was adjusted so that the slit-like opening 34B thereof was parallel to the first row composed of the plurality of needle-like recessed portions 15 formed in the surface of the mold 13. The nozzle 34 was pressed on the front surface of the mold 13 at a pressure (pressing force) of 0.14 kgf/cm$^2$ (1.4N/cm$^2$) at a position 2 mm away from the first row in a direction opposite to the second row. The pressing force was checked with the load cell 53. While the nozzle 34 was pressed, the liquid medicine 22 was discharged from the opening 34B for ten seconds at a discharge rate of 0.31 μL/sec while the nozzle 34 was moved in the filling movement direction at a movement speed of 1 mm/sec.

The movement of the nozzle 34 was stopped at a position 2 mm away from the tenth row of the arrayed needle-like recessed portions 15 in a direction opposite the ninth row 9 of the arrayed needle-like recessed portion 15, and then the nozzle 34 was removed from the mold 13.

Subsequently, the liquid medicine 22 which had been filled in the mold 13 was dried and solidified under conditions having a temperature of 20° C. and a relative humidity of 60% RH, and then all of the dried and solidified liquid medicines 22 adhering to the flat surface portions 13A other than the needle-like recessed portions 15 of the mold 13 were peeled off by using a pressure-sensitive adhesive tape.

Base Material Liquid Filling Step

Next, the base material liquid 24 was directly applied on the front surface of the mold 13 in which the liquid medicine 22 was dried and solidified by using a dispenser, and then was dried and solidified for 12 hours to form the polymer sheet 1.

Releasing Step

Subsequently, the polymer sheet 1 was released from the mold 13 to manufacture a transdermal absorption sheet.

Then, medicine content was measured for the acquired transdermal absorption sheet and the pressure-sensitive adhesive tape above with the following method.

Measurement of Medicine Content

The formed transdermal absorption sheet was completely re-dissolved in water of 3 mL to form a re-dissolved solution. Then, concentration of Evans blue dye in the formed re-dissolved solution was measured with an absorptiometer (V670 of JASCO Corp.), and filling amount of the liquid medicine 22 was calculated from an existing relationship between a concentration of Evans blue (calibration curve) and an absorbance. Likewise, a re-dissolved solution was formed also for the pressure-sensitive adhesive tape described above, and the re-dissolved solution was measured with the absorptiometer to calculate an amount of the liquid medicine 22 which had adhered to the flat surface portions 13A other than the needle-like recessed portions 15 of the mold 13.

Test Result

Test results are shown in the table of FIG. 18. In FIG. 18, a "holding method" indicates a method of holding the nozzle 34 to the Z-axis drive unit 50. In addition, "a number of repeated times" indicates a number of times that the filling operation of filling the needle-like recessed portions 15 of the mold 13 with the liquid medicine 22 was performed while the Z-axis drive unit 50 brought the nozzle 34 into pressed contact with the surface of the mold 13. The test was performed by repeating the filling operation five times in both Example 1 and Comparative Example 1. The filling amount into the needle-like recessed portions 15 was calculated by the measurement method described above.

As illustrated in FIG. 18, as a result of repeating the filling operation five times in Comparative Example 1, a minimum filling amount was 2.60 mg, a maximum filling amount was 3.55 mg, and a variation range was 0.95 mg.

In contrast, as a result of repeating the filling operation five times in Example 1, a minimum filling amount was 2.82 mg, a maximum filling amount was 3.21 mg, and a variation range was 0.39 mg, and thus the variation range was reduced to a half or less compared to that of Comparative Example 1.

That is, holding the nozzle 34 to the Z-axis drive unit 50 configured to vertically move the nozzle 34 through the elastic body 42 in order to bring the nozzle tip 35 into contact with the surface of the mold 13 with the nozzle tip 35 pressed to the mold, like Example 1, enables the elastic body 42 to absorb the variation in pressing force by the nozzle 34 caused by variation in displacement amount by pressing by the nozzle tip 35 on the surface of the mold 13 and variation in thickness of the mold and so on. Thus, the pressing force can be made uniform (constant).

As a result, the filling accuracy of the liquid medicine 22 for each of the needle-like recessed portions 15 can be improved.

What is claimed is:

1. A method of manufacturing a sheet with needle-like protrusions comprising:
    a preparing step of preparing a mold with needle-like recessed portions, a filling device provided with a liquid feeder having a nozzle that discharges a liquid from a slit-like opening formed at a nozzle tip; and
    a liquid filling step of filling the needle-like recessed portions with the liquid by repeating the following: a filling operation of supplying the liquid to the mold from the liquid feeder to fill one or more needle-like recessed portions with the liquid while the nozzle tip adjusted to a position above the needle-like recessed portions is brought into pressed contact with a surface of the mold; and a moving operation of moving the nozzle relatively to the mold in a state where the nozzle tip and the surface of the mold are in contact with each other, wherein
    the liquid filling step includes bringing the nozzle tip into pressed contact with the surface of the mold while the nozzle is held and supported by a Z-axis drive unit through an elastic body, wherein the Z-axis drive unit is configured to vertically move the nozzle through the elastic body.

2. The method of manufacturing a sheet according to claim 1, wherein a viscous substance is provided between the Z-axis drive unit and the nozzle.

3. The method of manufacturing a sheet according to claim 2, wherein the elastic body and the viscous substance are provided in parallel.

4. The method of manufacturing a sheet according to claim 1, wherein the elastic body has elastic force against translational movement in a thickness direction of the mold.

5. The method of manufacturing a sheet according to claim 4, wherein the elastic body is a coil spring.

6. The method of manufacturing a sheet according to claim 1, wherein the elastic body has both elastic force against translational movement in a thickness direction of the mold, and elastic force against in-plane rotation including a direction of relative movement between the nozzle and the mold.

7. The method of manufacturing a sheet according to claim 6, wherein the elastic body is a leaf spring.

8. The method of manufacturing a sheet according to claim 1, wherein a guide mechanism for regulating a movable range of the nozzle in a movement direction is further provided.

9. The method of manufacturing a sheet according to claim 1, wherein the sheet is a transdermal absorption sheet with needle-like protrusions containing a medicine.

10. A method of manufacturing a sheet with needle-like protrusions comprising:
    a preparing step of preparing a mold with needle-like recessed portions, a filling device provided with a liquid feeder having a nozzle that discharges a liquid from a slit-like opening formed at a nozzle tip; and
    a liquid filling step of filling the needle-like recessed portions with the liquid by repeating the following: a filling operation of supplying the liquid to the mold from the liquid feeder to fill one or more needle-like recessed portions with the liquid while the nozzle tip adjusted to a position above the needle-like recessed portions is brought into pressed contact with a surface of the mold, and a moving operation of moving the nozzle relatively to the mold in a state where the nozzle tip and the surface of the mold are in contact with each other, wherein
    the mold is placed on a suction base provided with an elastic body, and
    the liquid filling step includes bringing the nozzle tip into pressed contact with the surface of the mold by a Z-axis drive unit configured to vertically move the nozzle through the elastic body.

* * * * *